US012723931B2

(12) United States Patent
Greenhalgh et al.

(10) Patent No.: US 12,723,931 B2
(45) Date of Patent: Sep. 1, 2026

(54) ELECTROSURGICAL INSTRUMENT CALORIMETER AND METHOD FOR MEASURING AN ELECTROMAGNETIC POWER OUTPUT OF AN ELECTROSURGICAL INSTRUMENT

(71) Applicant: Creo Medical Limited, Chepstow (GB)

(72) Inventors: Alex Greenhalgh, Chepstow (GB); John Bishop, Chepstow (GB); Christopher Hancock, Chepstow (GB)

(73) Assignee: Creo Medical Limited, Chepstow (GB)

( * ) Notice: Subject to any disclaimer, the term of this patent is extended or adjusted under 35 U.S.C. 154(b) by 323 days.

(21) Appl. No.: 18/282,766

(22) PCT Filed: Mar. 15, 2022

(86) PCT No.: PCT/EP2022/056752
§ 371 (c)(1),
(2) Date: Sep. 18, 2023

(87) PCT Pub. No.: WO2022/194895
PCT Pub. Date: Sep. 22, 2022

(65) Prior Publication Data

US 2024/0167895 A1 May 23, 2024

(30) Foreign Application Priority Data

Mar. 19, 2021 (GB) ..................................... 2103841

(51) Int. Cl.
*A61B 18/18* (2006.01)
*G01K 17/00* (2006.01)
(Continued)

(52) U.S. Cl.
CPC ........ *G01K 17/003* (2013.01); *A61B 18/1815* (2013.01); *A61B 2018/00779* (2013.01);
(Continued)

(58) Field of Classification Search
CPC ........... H01P 1/262; A61B 2017/00725; A61B 18/815; A61B 2018/00577;
(Continued)

(56) References Cited

U.S. PATENT DOCUMENTS 2,560,536 A * 7/1951 Althouse ................ H01P 1/262 324/95
5,015,943 A * 5/1991 Mako .................. G01K 17/003 374/E17.002

(Continued)

FOREIGN PATENT DOCUMENTS

EP 0150253 A2 8/1985
JP 2003530976 A * 10/2003 .............. A61N 5/02

(Continued)

OTHER PUBLICATIONS

Computer translation of KR_20100067943_A (Year: 2025).*

(Continued)

*Primary Examiner* — Randy W Gibson
(74) *Attorney, Agent, or Firm* — Wolf, Greenfield & Sacks, P.C.

(57) ABSTRACT

The invention relates to an electrosurgical instrument calorimeter for measuring an electromagnetic energy output of an electrosurgical instrument powered by a generator, comprising a calorimeter cell for containing an absorption material configured to absorb electromagnetic radiation, at least one temperature sensor configured to measure a temperature of the absorption material, and a support structure configured to hold the electrosurgical instrument in such a position that electromagnetic radiation emitted by the electrosurgical instrument is absorbed by the absorption material.

28 Claims, 12 Drawing Sheets

(51) Int. Cl.
*A61B 18/00* (2006.01)
*G01J 5/06* (2022.01)
*G01J 5/58* (2022.01)
*H01P 1/26* (2006.01)

(52) U.S. Cl.
CPC ....... *A61B 2018/1823* (2013.01); *G01J 5/064* (2022.01); *G01J 5/58* (2013.01); *H01P 1/262* (2013.01)

(58) Field of Classification Search
CPC ........... A61B 2018/00589; A61B 2018/00601; A61B 2018/1823; A61B 8/14; A61B 2018/00791; A61B 2018/00779; G01K 17/003; G01J 5/58; G01J 5/064
See application file for complete search history.

(56) References Cited

U.S. PATENT DOCUMENTS 6,228,082 B1 * 5/2001 Baker ................ A61B 18/1482 606/49
6,629,974 B2 * 10/2003 Penny ...................... H05H 1/46 606/41
6,648,503 B2 * 11/2003 Tanaka ................. G01K 17/006 374/E17.002
6,723,091 B2 * 4/2004 Goble ...................... H05H 1/46 606/49
7,335,199 B2 * 2/2008 Goble ...................... H05H 1/24 606/49
7,785,322 B2 * 8/2010 Penny .................. A61B 18/042 606/41
2003/0099276 A1 * 5/2003 Argenti ................ G01K 17/003 374/E17.002
2005/0222556 A1 * 10/2005 Ariura .................... A61B 18/20 606/12
2006/0189974 A1 * 8/2006 Penny .................. A61B 18/042 606/41

FOREIGN PATENT DOCUMENTS

JP 2005287672 A * 10/2005 ............. A61B 18/20
JP 2009294069 A * 12/2009
JP 2010-261908 A 11/2010
KR 10-2010-0067943 A 6/2010
WO WO-0180949 A1 * 11/2001 ............... A61N 5/02
WO 2013177677 A1 12/2013
WO WO-2021113561 A1 * 6/2021 ........... A61B 18/042

OTHER PUBLICATIONS

"Chapter 9.6: Calorimetry" from the Libretexts: Chemistry webpage at <https://chem.libretexts.org/Bookshelves/General_Chemistry/Book%3A_General_Chemistry_-_An_Atoms_First_Approach_(Halpern)/Unit_4%3A_Thermochemistry/Chapter_9%3A_Thermochem/Chapter_9.6%3A_Calorimetry> (Year: 2025).*
Computer translation of JP 2009294069 A (Year: 2026).*
Japanese Office Action issued Aug. 5, 2025, in connection with Japanese Application No. 2023-557201, with English translation thereof.
International Search Report and Written Opinion dated Jun. 21, 2022, in connection with International Application No. PCT/EP2022/056752.
British Search Report dated Dec. 14, 2021, in connection with British Application No. GB 2103841.9.
Japanase Decision of Refusal proposed Jan. 20, 2026, for Japanese Application No. 2023-557201, with English translation thereof.

* cited by examiner

ELECTROSURGICAL INSTRUMENT CALORIMETER AND METHOD FOR MEASURING AN ELECTROMAGNETIC POWER OUTPUT OF AN ELECTROSURGICAL INSTRUMENT

RELATED APPLICATIONS

This Application is a national stage filing under 35 U.S.C. 371 of International Patent Application No. PCT/EP2022/056752, filed Mar. 15, 2022, entitled ELECTROSURGICAL INSTRUMENT CALORIMETER AND METHOD FOR MEASURING AN ELECTROMAGNETIC POWER OUTPUT OF AN ELECTROSURGICAL INSTRUMENT, which claims priority to United Kingdom Application No. 2103841.9, filed on Mar. 19, 2021, each of which is herein incorporated by reference in its entirety.

FIELD OF THE INVENTION

The invention relates to an electrosurgical instrument calorimeter for measuring an electromagnetic power output of an electrosurgical instrument powered by a generator. Further, the invention relates to a method for measuring an electromagnetic power output of the electrosurgical instrument powered by a generator.

BACKGROUND TO THE INVENTION

A modern approach to human surgery involves the use of microwave power of typically, but not limited to, 10 W-1000 W being delivered endoscopically, laparoscopically, or otherwise using a microwave power source, exemplified by the Creo Medical Ltd. CROMA™ generator, and often abbreviated to simply, 'generator', and a surgical instrument, exemplified by Creo Medical Ltd. MicroBlate™ and often abbreviated to simply, 'instrument' or 'electrosurgical instrument'.

At the command of the surgeon, microwave power is supplied by a generator either as a continuous wave (CW) or in bursts of short pulses for periods of up to a few minutes in order to affect a clinical outcome at the target site, for example: ablation/coagulation or cutting (resecting or dissecting) of tissue. To achieve consistent surgical effects, it is necessary to know that the amount of power being emitted by the instrument conforms to its design specification. While it is possible to dynamically monitor the amount of power supplied by a generator, and indeed reflected back into the generator by, e.g., a load mismatch or poor connection, there is not currently any readily available means of measuring the amount of power emitted at the surgical instrument tip. For example, there may be unknown damage to, or some other variation in the electrical coupling of connecting cables. Material variations during the manufacture of instruments may also lead to higher or lower microwave attenuation (loss) than specified being incorporated into an instrument, perhaps causing unwanted heating of the connecting cable rather than the target tissue. In these cases, the surgical instrument might deliver an inconsistent power level to the target tissue and cause undesirable effects for the surgeon.

SUMMARY OF THE INVENTION

At its most general, the present invention provides an electrosurgical instrument calorimeter which can be used for measuring an electromagnetic energy output of the electrosurgical instrument that is powered by a generator. In addition, this invention provides a method for measuring the electromagnetic energy output of the electrosurgical instrument using a calorimeter.

While there is no straightforward method of detecting power emitted by an instrument during surgery itself, it is proposed that a microwave surgical instrument calorimeter, as described here, may be used during manufacture and verification-and-validation (V&V) exercises to ensure the instrument assemblies are performing, or are likely to have performed in a post-operative situation, to their designed value.

While there are many methods available of measuring regular, free-space antenna performance, as exemplified by commonly used microwave anechoic chamber apparatus, the instruments used in microwave electrosurgery rely on the instrument delivering power into an absorptive, non-air medium: normally body tissue. Body tissue is largely comprised of water and readily absorbs microwave power, which is the principle on which microwave electrosurgery is based. However, this total radiated power absorption in a lossy medium (water) means that regular free-space antenna pattern measurements will not work. In free space the instrument tip may present a large impedance mismatch compared with being in tissue and the radiated power would be radically different to that when in contact with tissue. Also, in free space, the radiation pattern of an antenna is largely governed by the far-field pattern whereas in a lossy medium the near-field pattern is more significant, especially through capacitive coupling of power into the medium.

It is here proposed that to support manufacture and V&V activities, a water or other liquid-based calorimeter is constructed as a tissue-analog in order to measure the temperature rise of the liquid when microwave power is applied for a known duration of time to an instrument suspended in the liquid. By measuring or knowing the duration that power is supplied to a known mass of liquid and subsequently measuring the temperature rise of the liquid it is possible to convert this using the specific heat capacity of the liquid to estimate the amount of energy delivered into it and the average power delivered by the instrument. This would facilitate quantitative performance analyses, such as, but not limited to:

- Instruments to be compared with simulated performance data;
- Instruments to be improved by understanding how much power is being lost between the generator and the distal end of the instrument;
- Batch checking to ensure reliability of manufacturing processes;
- Post-operative instrument quality checking to gauge that an instrument has not become defective during use;
- Destructive or non-destructive instrument research and development;
- General validation and verification;
- Automated testing of electrosurgical instruments through industry-standard and proprietary control protocols, such as the Creo Medical Kamaptive™ protocol;
- Comparative analysis with alternative or competing technology from other manufacturers;
- Measurement of instruments that may deliver a diversity of electromagnetic frequencies either simultaneously or sequentially; and/or
- In combination with a heat sensitive or electromagnetic-field sensitive material around the instrument tip, assess the amount of power transmitted at various points on the radiation pattern surface of the instrument.

There are various types of calorimeters available on the market, chiefly: bomb calorimeters and reaction calorimeters. A bomb calorimeter measures the number of calories in a substance, for example in food, by the controlled combustion of such substances and measurement of the temperature increase. A reaction calorimeter measures power output from chemical reactions, again by measuring the temperature change. Neither of these versions of a calorimeter are particularly suitable for measuring the power output of an electrosurgical instrument. However, the specially designed electrosurgical instrument calorimeter is to account for heat-absorption by the instrument itself, for a variety of instrument types and sizes, and may be remotely controlled (e.g., by network connection) for automated testing.

An electrosurgical instrument calorimeter is provided for measuring the electromagnetic energy and/or power output of the electrosurgical instrument powered by generator. The electrosurgical instrument calorimeter comprises a calorimeter cell, at least one temperature sensor, and a support structure. The calorimeter cell is configured to contain an absorption material configured to absorb electromagnetic radiation emitted by the electrosurgical instrument. The at least one temperature sensor is configured to measure the temperature of the absorption material, in particular a temporary change of the absorption material. The support structure is configured to hold the electrosurgical instrument in such a position that electromagnetic radiation emitted by the electrosurgical instrument is absorbed by the absorption material. In an embodiment, the position ensures that a majority, entirety or substantial portion of the electromagnetic radiation emitted by the electrosurgical instrument is absorbed by the absorption material, for example, all electromagnetic radiation emitted by the electrosurgical instrument is completely absorbed by this absorption material.

The electromagnetic energy output corresponds to the energy of the electromagnetic radiation emitted by the electrosurgical instrument. The electromagnetic power output is the power of the electromagnetic radiation which is emitted by the electrical surgical instrument for treating tissue at the target site. The electromagnetic power output is the electromagnetic energy output divided by the time of emission of the electromagnetic radiation. The electrosurgical instrument calorimeter may be configured to measure the electromagnetic energy output and/or the electromagnetic power output.

The electromagnetic radiation may be radio frequency radiation, and/or microwave radiation, mm-wave radiation, and/or infrared radiation. The energy for the electromagnetic radiation is generated by a generator and transmitted to the electrosurgical instrument, for example by one or more cables such as coaxial cables. Thus, the generator is a power source for generating the electromagnetic power, while the electrosurgical instrument emits the electromagnetic power into the target site. The generator, the electrosurgical instrument, and/or the cable may form an electrosurgical apparatus. As discussed above, the electromagnetic power may be used for coagulating or cutting tissue.

The electrosurgical instrument may be a scoping device which can be inserted into a body cavity. In particular, a distal end of the electrosurgical instrument may be inserted into the body cavity for treating a target tissue. In this case, the electrosurgical instrument may include an instrument tip at which the electromagnetic power is radiated or transmitted into the target tissue at the target site for obtaining the desired treatment effect. Alternatively, the electrosurgical instrument may include a waveguide having an energy output port which is to be arranged above tissue to be treated, such as skin tissue. The electromagnetic radiation exiting the waveguide at the energy output port impinges on the tissue to be treated for providing the desired treatment effect.

The electrosurgical instrument calorimeter is a device for absorbing the electromagnetic radiation emitted by the electrosurgical instrument and converting it into heat. The thereby induced temperature change is measured for calculating the energy and/or power emitted by the electrosurgical instrument.

In an optional embodiment, the electrosurgical instrument calorimeter includes a calorimeter base, wherein further optionally the calorimeter cell is attached to the calorimeter base.

The calorimeter base may include a housing and forms the base structure to which other components of the electrosurgical instrument calorimeter are attached. The housing may provide the outer surface of the electrosurgical instrument calorimeter. The calorimeter base and/or the housing may be made from a plastic material or a metal.

The calorimeter cell is configured to receive and contain the absorption material which is provided for absorbing the electromagnetic radiation emitted by the electrosurgical instrument. The heat capacity of the absorption material needs to be known and is used for calculating the electromagnetic power output of the electrosurgical instrument.

The absorption material may be or comprise a liquid, a powder of solid particles (e.g. a granular material), a solid, a gas and/or a plasma. Liquid may be the preferred embodiment of the absorption material since it has good absorption properties in the frequency range usually emitted by the electrosurgical instrument and a heat capacity beneficial for the calorimeter measurements. In the following, for ease of understanding, a referral to "liquid" should be understood as generally referring to the absorption material if applicable.

In operation at microwave frequencies, the liquid type may be water of an appropriate purity. The choice of liquid is not limited to any one type but should be of a type that is similar to the impedance of the tissue with which that the instrument is normally used. If an instrument that delivers infra-red energy is used, then it may be appropriate to fill the cell container with a suitable infra-red absorbing substance, rather than pure water that allows a high degree of transmission of infra-red light. Similarly, if the instrument is to deliver low-frequency RF power of around 400 kHz, then it may be appropriate to use a saline solution that is electrically conductive.

The calorimeter cell may be permanently or releasably fixed to the calorimeter base. For example, the calorimeter cell is arranged in a hole or socket of the housing. The calorimeter cell has an opening through which the liquid can be inserted into the calorimeter cell. Their overall configuration of the calorimeter cell may be that of a beaker or a cup.

The calorimeter cell may be heat-insulated to reduce the loss of heat since heat loss adversely affect the measurement of the electromagnetic power output of the electrosurgical instrument. In other words, the heat insulation of the calorimeter cell is provided such that the temperature change induced by the absorption of the electromagnetic radiation emitted by the electrosurgical instrument is not significantly distorted by heat losses of the calorimeter cell.

One or more temperature sensors are provided for measuring the temperature of the liquid. The temperature sensor may be in contact with the liquid. Various different types of temperature sensors may be used, for example a thermistor or other thermal transducers. The temperature sensor may be configured to continuously measure the temperature of the liquid.

The support structure is configured to hold and/or support the electrosurgical instrument in such a position that the electromagnetic radiation emitted by the electrosurgical instrument is absorbed by the liquid in the calorimeter cell. Optionally, the electromagnetic radiation emitted by the electrosurgical instrument is completely or almost completely absorbed by the liquid. To this end, the support structure may be configured to releasably hold and/or support the electrosurgical instrument. This means, during measurement, the electrosurgical instrument is attached to the support structure in a position in which that that part of the electrosurgical instrument which emits electromagnetic radiation is positioned within the liquid or directly above the liquid. For example, the support structure holds the electrosurgical instrument in such a way that the instrument tip is fully inserted in the liquid. If the electrosurgical instrument includes a waveguide, the energy output port is positioned close to or in contact the liquid by the support structure such that substantially all the electromagnetic radiation emitted at the energy output port impinges on the liquid. The energy output port could be an opening in the waveguide. This waveguide opening may be covered with a cover whose material is transparent to the electromagnetic radiation propagating within the waveguide.

In an optional embodiment, the calorimeter cell includes a cell housing fixedly or permanently attached to the calorimeter base, an attachment configured to be releasably attached to the cell housing, and a cell container configured to receive the liquid and arranged within the cell housing.

The cell housing, the attachment and the cell container may be concentric to each other such that they can be inserted into each other. In general, the components of the calorimeter cell may be concentric such that they can be coaxially inserted into each other.

The cell housing acts as a receptacle for holding the attachment. The cell housing may be a blind hole or socket in the housing and may be fluid tight. The cell housing may include attachment means for releasably attaching the attachment to the cell housing. The attachment may also comprise corresponding attachment means which engage with the attachment means of the cell housing. The cell housing may protrude from the surface of the housing or is flush with the housing.

The attachment may be permanently fixed to the cell housing such that the attachment and the cell housing form a unitary component. However, the cell housing may be detachable from the attachment. The attachment including the cell container may be inserted into the cell housing.

The attachment and/or the cell container may be formed as a receptacle, beaker, or cup wherein the cell container is inserted into attachment so that the free openings of both the attachment and the cell container form a common outer surface. Optionally, the cell container and the attachment define a gap therebetween and the area of connection between the cell container and the attachment is small in order to reduce heat transmission via the connection area. For example, the cell container has an outer collar at its opening which engages with an inner collar of the attachment. The inner collar and the outer collar may extend around the complete circumference and form the only connection between the attachment and the cell container. Alternatively, the inner collar and the outer collar extend only over one or more sections along the circumference. For example, the inner collar and the outer collar include two connection means arranged opposing each other.

The cell container may sit permanently inside the top of the attachment and holds a known, fixed mass of liquid which will be heated by the electrosurgical instrument. The cell container may have a low mass to reduce the amount of thermal energy absorbed from the liquid. It also may be waterproof and be able to insulate the liquid, reducing the amount of thermal energy dissipated into the surroundings by radiation. A vacuum-flask arrangement could equally be used but a mechanically thin plastic insulating material is preferred due to its durability, low thermal mass, and rigidity. The attachment and/or the cell container may have a reflective inner surface for containing the electromagnetic radiation emitted by the electrosurgical instrument and/thermal radiation within the calorimeter cell.

The cell housing and/or the attachment may be made from a metal and/or lightweight plastic material.

In optional embodiment, the cell housing and/or the cell container provide heat insulation for the liquid.

The heat insulation may be provided by the above-described vacuum-flask arrangement in which, for example, a space between the attachment and the cell container is evacuated. Alternatively, the space between the cell container and the attachment may be filled with a heat insulating material.

It is also possible that a plurality of differently sized cell containers is provided which each are supported by the same attachment. In this way, the size of the cell container can be chosen to contain an amount of liquid which is chosen to the size and energy emission of the electrosurgical instrument while the differently sized cell containers can each be inserted into the cell housing by means of the adapter. This simplifies the measurement of different types of electrosurgical instruments.

In optional embodiment, the at least one temperature sensor is arranged in and/or on the cell container.

The temperature sensor may be arranged exposed on an inner surface of the cell container such that the sensor is in contact with the liquid. Alternatively, the temperature sensor may be supported by the cell container such that the temperature sensor is arranged within the liquid. Optionally, two or more temperature sensors are provided which are distributed in a space defined by the cell container. The presence of a plurality of temperature sensors increases the accuracy of the temperature measurement since it is possible to detect whether the liquid as a homogenous temperature distribution.

The temperature sensor may be an electrical temperature sensor and includes wires for providing the electrical connection to the temperature sensor. The wires may extend within the space defined by the cell container and the attachment. For example, the temperature sensor is arranged within the wall of the cell container such that one side of the temperature sensor is in contact with the liquid and the other side of the temperature sensor is connected to the wire and faces the space defined by the cell container and the attachment.

In an optional embodiment, the calorimeter cell includes a first electrical connector attached to the cell housing and a second electrical connector attached to the attachment and in electrical connection with the at least one temperature sensor, wherein optionally, the insertion of the attachment into the cell housing connects the second electrical connector of the first electrical connector.

The first electrical connector may be a socket while the second electrical connector may be a plug or vice versa. The first electrical connector may be arranged in a bottom surface of the cell housing while the second electrical connector can be also arranged within a bottom surface of the attachment. Upon inserting the attachment into the cell housing, the second electrical connector is connected to or inserted into the first electrical connector. Optionally, the first electrical connector and the second electrical connector also provide mechanical connection between the cell housing and the attachment, optionally the sole mechanical connection between the cell housing and the attachment.

Wires may be connected to the first electrical connector for providing an electrical connection between the first electrical connector and a controller to be described later. The second electrical connector may be electrically connected to the temperature sensor via one or more wires.

In an optional embodiment, the calorimeter cell further includes a lid for closing the calorimeter cell, wherein optionally the lid includes a passageway for inserting the electrosurgical instrument into the liquid.

The lid may be configured to only close the opening of the cell container or the cell container and the attachment. For example, the lid may be arranged on the cell container or the combination of the cell container and the attachment. Preferably, the lid has a base portion and an outer wall wherein, in the closed position, the outer wall surrounds the cell container and/or the attachment while the base portion rests on the cell container and or the attachment. In this case, the outer wall may (additionally) rest on the housing and/or the cell housing.

Optionally, the lid is made from a material with low heat capacity and/or includes a reflective surface. In addition, the lid may be hollow to increase the heat insulation effect. These aspects help to reduce the loss of heat from the calorimeter cell. The at least one temperature sensor or some of the temperature sensors may be supported by the lid, for example, one or more temperature sensors may be directly or indirectly connected to the lid. Upon placing the lid on the calorimeter cell, the temperature sensor is immersed into the liquid. This embodiment does not require the first and second electrical connector at the calorimeter cell since the electronic connection between the at least one temperature sensor and the controller may be routed through the lid. Instead, the first and second electrical connector may be arranged on the housing and on the lid. For example, the second electrical connector is inserted into the first electrical connector when the lid is placed on the calorimeter cell.

Preferably, the power output of the electrical surgical instrument is measured with the lid on the calorimeter cell. Therefore, the lid may include a passageway through which the electrical surgical instrument can be passed. Optionally, the dimensions of the passage correspond to the dimensions of the electrosurgical instrument such that there is no or only a minor gap between an inner surface of the pass where its way and an outer surface of the electrosurgical instrument. A plurality of lids may be provided whereby each lid has a passageway of different dimensions whereby the passageway of each lid may be aligned to an electrosurgical instrument to be measured.

In optional embodiment, the electrosurgical instrument calorimeter further comprises a stirrer for stirring the liquid, wherein optionally the stirrer is attached to the lid.

The stirrer is provided for evenly distributing the heat generated in the liquid. For example, the stirrer disperses the heat generated by the instrument tip around the liquid, preventing heat pockets from forming. The stirrer may mix the liquid both vertically and horizontally as well as may have a low mass so as to reduce the amount of thermal energy it takes from the liquid, and a speed that is low enough that the frictional energy imparted to the liquid is insignificant compared with the energy to be measured. Through software and calibration, the calorimeter may be able to calibrate and subtract the mechanical frictional energy component that is imparted to the liquid from the final power and energy results, making the overall measurement more accurate.

The stirrer may be a stiff helical wire or a miniature impeller. Other types of stirrer might include but are not limited to magnetically coupled or ultrasonic stirrers. With the goal of minimising overall thermal mass and the frictional movement energy imparted to the liquid the preferred embodiment may use a lightweight mechanical stirrer.

The stirrer may be supported by the lid. Thus, the stirrer may rotate with respect to the lid. The lid may include means for rotatably supporting the stirrer, in particular an axis of the stirrer. The stirrer may be arranged offset to the passageway but close enough to the passageway such that the stirrer distributes the heat generated by the electrosurgical instrument.

In optional embodiment, the electrosurgical instrument calorimeter includes a motor for moving the stirrer.

The motor may be an electrical motor and may generate a rotational movement for rotating the stirrer. The motor may be arranged in such a position that the heat generated by the motor does not increase the temperature of the liquid. To this end, the motor may be covered by heat insulating material.

In optional embodiment, the cell housing further includes a motor bracket for supporting the motor.

The motor bracket may be arranged on an outer surface of the cell housing. The motor bracket may be any means for attaching the electrical motor to the cell housing.

In optional embodiment, the lid includes a transmission device for transmitting a motion of the motor to the stirrer.

For example, the transmission device may transmit the rotation of the motor to rotate the stirrer. The transmission device may include one or more gears, cogs and/or belt drives for transmitting the rotation of the electric motor to the axle of the stirrer. Alternatively or additionally, the transmission device includes magnetic coupling of the motor to the stirrer. The transmission device may magnetically couple the rotation of the motor to the stirrer. The transmission mechanism may be contained within the lid such that the transmission mechanism is not visible from the outside.

In an optional embodiment, the electrosurgical instrument calorimeter further comprises a stirrer motor configured to move the calorimeter cell for stirring the liquid or the powder.

The stirrer motor may be an electrical motor and may be attached to the calorimeter base. In this case, the stirrer motor may rotate and/or move the complete calorimeter cell. In another embodiment, the stirrer motor may be attached to the cell housing and configured to rotate the attachment and, thus, the cell container. In this case, the attachment may be releasably coupled to the stirrer motor. For example, when inserting the attachment into the cell housing, the attachment is coupled to the stirrer motor such as the axle of the stirrer motor. In another embodiment, a spinning disk is provided which is attached to an axle of the stirrer motor. The calorimeter cell, the attachment, or the cell container itself may be attached (e.g. releasably) to the spinning disk. For example, the spinning disk may include one or more fasteners for releasably fastening the calorimeter cell, the attachment, or the cell container to the spinning disk.

For example, the stirrer motor may rotate the attachment within the cell housing. However, the stirrer motor may be configured to shake, agitate or spatially move the calorimeter cell such as a back-and-forth movement. The stirrer motor may produce linear or rotary force (torque).

The cell container may include stirring means which convert the movement of the cell container into movement of the liquid. The stirring means may include one or more stirring objects that are steady with respect to the movement of the cell container such that the liquid in the cell container moves relative to the stirring objects resulting in a stirring of the liquid. For example, the stirring object is attached to the lid and may have the shape of a paddle. The temperature sensor may be arranged on the stirring object. Alternatively or additionally, the stirring objects may be attached to the cell container. For example, the cell container may include protrusions which protrude from the inner surface of the cell container into the liquid. Further alternatively or additionally, the stirring means are provided by the shape of the cell container. For example, the cell container may have a rotationally non-symmetrical shape such that a rotation of the cell container results in stirring of the liquid. The cell container may have ramp-shaped bottom surface (e.g. forming a step) which stirs the liquid when the cell container is moving.

The liquid may be stirred by the electrosurgical instrument itself. To this end, the electrosurgical instrument is inserted into the liquid and held steady with respect to the movement of the calorimeter cell, for example by the support structure. In this case, the movement of the calorimeter cell induces a movement of the liquid which then moves relative to the electrosurgical instrument resulting in a stirring of the liquid.

The lid may be attached to the calorimeter base such that the calorimeter cell, in particular the attachment and the cell container, can move (rotate) with respect to the lid. The lid may not be in contact with the calorimeter cell, in particular the attachment and the cell container, allowing a movement or rotation of the calorimeter cell with respect to the lid.

In optional embodiment, the support structure is supported by the calorimeter base.

Optionally, the complete support structure or parts of the support structure may be permanently fixed to the calorimeter base. Thus, the support structure forms a part of the electrosurgical instrument calorimeter. This allows to have a fixed relationship between the support structure at the calorimeter cell simplifying the placement of the electrosurgical instrument in or above the liquid. The support structure may be fixed to the housing of the calorimeter base. Alternatively, the support structure may be not fixed to the calorimeter base or releasably fixed to the calorimeter base.

The support structure may include a robotic arm which is configured and/or controlled to place and/or support the electrosurgical instrument in or above the liquid in the calorimeter cell.

In optional embodiment, an instrument guide clamp is provided for holding the electrosurgical instrument in an upright position.

The instrument guide clamp is a means for releasably supporting or holding the electrosurgical instrument. The instrument guide clamp may include a clamp or bracket which can releasably engage with a portion of the electrosurgical instrument. The instrument guide clamp is provided for maintaining the orientation of the electrical surgical instrument and/or for supporting the electrosurgical instrument during measurement. In particular, the instrument guide clamp of the support structure may be the only mechanical means for holding the electrosurgical instrument in or above the liquid during measurement. Alternatively, the instrument tip may be held by another mechanical means described later while the instrument guide clamp is provided for supporting a cable or a flexible part of the electrosurgical instrument.

In optional embodiment, a stand is provided for supporting the instrument guide clamp, wherein optionally the stand is attached to the calorimeter base.

The stand may be a rod, bar or pole which protrude from the calorimeter base, in particular from its housing. The stand may have a vertical orientation. The instrument guide clamp may horizontally protrude from the stand. The instrument guide clamp may be configured to be detachably fixed to the stand. For example, the instrument guide clamp may be attached to the stand at various heights. The stand and the instrument guide clamp may form a boom.

The instrument guide clamp may include two attachment portions: the first attachment portion is for releasably fixing the electrosurgical instrument to the instrument guide clamp while the second attachment portion is for releasably fixing the instrument guide clamp to the stand.

In an optional embodiment, the electrosurgical instrument calorimeter further comprises a depth gauge mechanism for facilitating a repeatably consistent placement of the instrument tip of the electrosurgical instrument in the liquid.

The depth gauge mechanism may be used to accurately position the electrosurgical instrument with respect to the liquid. Thus, the depth gauge mechanism allows to position the electrosurgical instrument in the same position each time the electrosurgical instrument is subjected to a calorimetry measurement. This facilitates comparable measurements of the energy/power output of the electrosurgical instrument. In other words, the depth gauge mechanism facilitates the correct positioning of the electrosurgical instrument.

For example, the depth gauge mechanism allows to position the electrosurgical instrument in such a way that the instrument tip is fully immersed in the liquid while the parts of the electrosurgical instrument other than the instrument tip are not immersed in the liquid. In other words, the depth gauge mechanism allows to position the electrosurgical instrument such that only the instrument tip is in contact with the liquid.

In optional embodiment the depth gauge mechanism includes a depth gauge clamp which can be attached to the electrosurgical instrument and has an outer diameter larger than an inner diameter of the passageway. Optionally, the depth gauge mechanism further includes a depth gauge socket having a depth that corresponds to a distance between the distal end of the electrosurgical instrument and an upper surface of the lid in the repeatably consistent position of the electrosurgical instrument.

The depth gauge clamp may be a bracket, cylinder or clamp which can be releasably attached to the electrosurgical instrument. The mechanisms for attaching the depth gauge clamp to the electrosurgical instrument may be similar to the ones of the instrument guide clamp. The depth gauge clamp increases the diameter of the electrosurgical instrument such that the depth gauge clamp abuts against the lid when the electrosurgical instrument is inserted into the passageway of the lid.

The outer diameter and the inner diameter may refer to the longest extension within a cross-section of the depth gauge clamp and the passageway, respectively. In other words, the outer dimensions of the depth gauge clamp are such that the depth gauge clamp cannot be inserted into the passageway. As such, the depth gauge clamp acts as a stopper when inserting the electrical surgical instrument into the passageway. Thus, the distance between the distal end of the electrosurgical instrument to the position of the depth gauge clamp attached to the electrosurgical instrument determines how deep the electrosurgical instrument is inserted into the liquid. In other words, the point of attachment of the depth gauge clamp to the electrosurgical instrument determines the insertion depth of the electrosurgical instrument into the liquid.

The point of attachment may be reliably determined by using a depth gauge socket which may be a blind hole. To this end, the distal end of the electrosurgical instrument is inserted into the depth gauge socket until a distal end the electrosurgical instrument abuts against a bottom surface of the depth gauge socket. Then, the depth gauge clamp is attached to the electrosurgical instrument in such a way that the depth gauge clamp abuts against an outer surface of the depth gauge socket. This means, the depth of the depth gauge socket (the distance between the bottom surface of the depth gauge socket and the outer surface of the depth gauge socket) corresponds to the distance between the distal end of the electrosurgical instrument and the outer surface of the lid in a correct position of the electrosurgical instrument with respect to the liquid.

As the instrument tips of different electrosurgical instruments may have different lengths, a plurality of depth gauge sockets may be provided whereby each depth gauge socket indicates the correct positioning of the depth gauge clamp for a particular type of electrosurgical instrument.

In an optional embodiment, the depth gauge socket is arranged on the calorimeter base.

The depth gauge socket may be arranged in or on the housing of the calorimeter base. Alternatively or additionally, the depth gauge socket may be external to the calorimeter base. For example, various holes are drilled into a solid component providing a plurality of depth gauge sockets.

In an optional embodiment, the electrosurgical instrument calorimeter further comprises a controller configured to calculate the electromagnetic energy output of the electrosurgical instrument based on the measurement of the at least one temperature sensor.

The controller may include one or more microprocessors, one or more memories, and/or further electrical components for controlling the electrosurgical instrument calorimeter and analysing the results detected therewith. The controller may be attached to the calorimeter base and optionally arranged within the housing of the calorimeter base. However, the controller may be an external computer attached to the electrosurgical instrument calorimeter.

The controller may be connected to the at least one temperature sensor as described above. Optionally, the electrosurgical instrument calorimeter includes a display and/or a user interface (for example one or more buttons, dials, and/or switches) which are connected to the controller. The controller may control the display and receives inputs from the user interface. For example, the amount of liquid filled into the cell container as well as the heat capacity of the liquid may be input using the user interface. The display may be used for displaying the electromagnetic power output of the electrosurgical instrument.

The user display may be, for example, a 20-by-4 character alphanumeric or graphical display and may display the operational parameters of the apparatus, the results of any measurements, as well as brief instructions on how to operate the apparatus. The user interface may optionally be incorporated into a touch-sensitive screen for aesthetic or operational needs.

The controller may include a microcontroller and electronic circuitry that, through software, controls all aspects of calorimeter operation, including but not limited to: configuring operational parameters, timing of power delivery and sequencing of temperature measurements, acting on user interface commands, acting on and producing control events from and to the control connectors, controlling the timing and speed of the stirrer motor and converting the formats of all information to be displayed or conveyed to the user.

The controller may be configured to execute a calculation routine such as a software code for calculating the electromagnetic power output of the electrosurgical instrument. The calculation may be based on a temperature change of the liquid induced by the absorbed electromagnetic radiation emitted by the electrosurgical instrument. This temperature change may be measured by the temperature sensor and forwarded to the controller. The controller may start and/or end the temperature measurement by controlling the temperature sensor accordingly. The calculation of the electromagnetic power output may also factor in the amount of liquid within the cell container and the heat capacity of the liquid. Both parameters may be input using the user interface. Alternatively, these types of information may be electronically forwarded to the controller. In yet another embodiment, the amount of liquid within the cell container and the heat capacity of the liquid may be stored in the controller and are not changed between different measurements. Details of the calculation will be discussed below.

In optional embodiment, the controller is configured to control the motor.

To this end, the controller may be electronically connected to the motor to control the movement of the electric motor. For example, upon starting a measurement, the controller starts the movement of the electric motor. In addition, the controller may change the motion speed of the electric motor.

In an optional embodiment, the electrosurgical instrument calorimeter includes at least one control connector configured to provide an electrical connection of the controller to the generator.

The control connector may be attached to the housing of the calorimeter base and is connected to the controller by means of one or more wires. The control connector allows to provide an electrical and/or electronic connection between the controller and the generator. Thus, it is possible that the generator and the controller electronically communicate with each other. For example, the controller may acquire the intended electromagnetic power output of the electrosurgical instrument and/or the timespan during which the electromagnetic radiation is emitted by the electrosurgical instrument into the liquid. The former information may be compared to the electromagnetic power output measured using the electrosurgical instrument calorimeter. The latter information may be used for calculating the electromagnetic power output.

In an optional embodiment, the electrosurgical instrument calorimeter further comprises an external user interface connectable to the controller and/or the generator for starting the emission of the electromagnetic power output of the electrosurgical instrument and/or the measurement of the temperature of the liquid.

The external user interface may be a foot switch or other type of switch. The external user interface may be used to start the measurement period. The external user interface may generate a start signal upon its actuation.

The external user interface may be connected to the generator and/or to the controller for example via the control connector and/or a further connector. The start signal may be received by the generator and prompts the generation of electromagnetic power, for example for a predetermined time span. Alternatively or additionally, the start signal may be received by the controller and prompts the controller to start recording the temperature of the liquid.

It is however possible, that the start signal is received by the generator and forwarded to the controller or that a start signal is received by the controller and forwarded to the generator via the above-described connection between the controller and the generator. This means, the external user interface may only be connected to either the generator or the controller.

In a further optional embodiment, the start signal generated by the external user interface may only be received by the generator upon which the generation of electric magnetic power output is started. The controller may be configured to determine a temperature change such that the controller does not require an external start signal for the measurement but can determine the operation of the electrosurgical instrument.

The external user interface provides a simple starting mechanism of the measurement. In addition, the external user interface allows to coordinate the operation of the generator and of the electrosurgical instrument calorimeter.

In an optional embodiment, the electrosurgical instrument calorimeter may further comprise an automated test equipment system connected to the controller and connectable to the generator, wherein optionally the automated test equipment system is configured to communicate with the controller and/or the generator for performing automated calorimetry measurements.

The generator and electrosurgical instrument calorimeter may be connected into the automated test equipment (ATE) system, for example by wired Ethernet, Wi-Fi, Bluetooth, USB, or serial connection that supports a communication protocol. The protocol may be, for example, General Purpose Interface Bus (GPIB) or the Standard Commands for Programmable Instruments (SCPI), as are in common use, or a proprietary protocol such as the Creo Medical Kamaptive™ protocol.

The automated test equipment system may include a computer and/or a server which operates the automated calorimetry measurements. For example, the automated test equipment system may repeatedly measure the power output of the electrosurgical instrument which is an example of an automated calorimetry measurement. Furthermore, the automated test equipment system may control a robot or a robotic system of the support structure which can place different types of electoral surgical instruments into the fluid for calorimetry measurements.

This mode of operation facilitates unattended, programmed measurements that can be used for assessing reliability and repeatability, for example in validation and verification studies.

In optional embodiment, the electrosurgical instrument calorimeter further comprises a return electrode which is arranged in the cell container and, optionally, is electrically grounded.

The electrosurgical instrument calorimeter may be used, equally, with bipolar instruments and monopolar instruments. With bipolar instruments the electrical return path or electromagnetic counterpoise is normally the outer shield of a connecting coaxial cable or a separate electrode within the instrument tip assembly. For monopolar operation, a return electrode may be placed inside the cell container to make conductive contact between the liquid and the instrument tip. Bipolar instruments may also be used in monopolar mode along if a monopolar return electrode is connected in circuit. A monopolar return electrode may include thin foil, such as copper, silver, or gold, or deposited onto the surface of the cell container as a conductive coating.

The electrical grounding of the return electrode may be accomplished by a wire connected to the return electrode which may be connected to the housing or the surface on which the calorimeter base is arranged. Alternatively, the return electrode may be connected to a ground contact of the power supply line for powering the controller and/or temperature sensor.

In an optional embodiment, the electrosurgical instrument calorimeter further comprises a radiation detector arranged in the calorimeter cell and configured to detect electromagnetic radiation.

The radiation detector may be any detector which is capable of detecting electromagnetic radiation in the bandwidth of radiation which is emitted by the electrosurgical instrument. For example, the radiation detector may be configured to detect radio frequency radiation or microwave radiation. The radiation detector may be electrically connected to the controller.

The radiation detector may be arranged within the cell housing, within the attachment or with in the cell container. Preferably, the radiation detector is arranged above the liquid in the cell container.

The radiation detector is provided to detect whether or not the radiation emitted by the electrosurgical instrument is fully absorbed by the liquid. For example, if the instrument tip is not fully inserted into the liquid, not all radiation is absorbed by the liquid and, thus contributes to the heating of the liquid. Alternatively or additionally, the electrosurgical instrument may include leaks which emit electromagnetic radiation such that the power of the electromagnetic radiation that is generated at the generator does not correspond to the power that is emitted at the instrument tip. Thus, the detection of electromagnetic variation indicates a measurement artefact.

The controller may be configured to discard any measurements in which the intensity of the radiation detected by the radiation detector is above a certain threshold. Alternatively or additionally, the controller may be configured to prevent or stop the calorimeter measurement if the intensity of the detected radiation is above a certain safety threshold which indicates a potential hazard for a user by the electromagnetic radiation emitted by the electrosurgical instrument.

In an optional embodiment, the electrosurgical instrument calorimeter further comprises an ambient air temperature sensor configured to measure the temperature of the surrounding of the electrosurgical instrument calorimeter.

The ambient air temperature sensor may be arranged on the calorimeter base, in particular on or within its housing. The ambient temperature sensor may be exposed to the surroundings of the electrosurgical instrument calorimeter.

The temperature detected by the ambient temperature sensor may allow to quantify the energy loss in the liquid due to heat transmission from the liquid to the surroundings of the liquid. Since this type of heat loss is dependent on the temperature difference between the temperature of the liquid and the temperature of the surroundings, knowing the temperature of the surroundings may help to increase the measurement accuracy. To this end, the controller may be configured to calculate the energy or power emitted by the electrosurgical instrument based on the temperature of the surrounding of the electrosurgical instrument calorimeter. To this end, the ambient air temperature sensor may be electronically connected to the controller. The temperature of the surrounding may be continuously measured or at certain points of times of the measurement of the liquid temperature.

The air ambient temperature sensor can capture precise temperature measurements over a long period of time which presents the ability to record data about the environment of the electrosurgical instrument calorimeter. Addition of an ambient air temperature sensor can allow a correction factor to be applied throughout or after the measurement process to account for more rapid cooling in a cold ambient environment, thus improving the accuracy of the result.

In an optional embodiment, the electrosurgical instrument calorimeter further comprises a heat sensitive load material which is configured to be placed around the instrument tip of the electrosurgical instrument and which is configured to locally change the physical property upon irradiation of electromagnetic radiation, wherein optionally the heat sensitive load material is configured to locally change the physical property depending on the strength and/or the duration of the electromagnetic radiation.

The heat sensitive load material may include a heat-sensitive gel, tape and/or other material indicator that may be placed around the instrument's radiating tip prior to power delivery into the calorimeter. This could provide information on the distribution of the energy profile around the geometry of the instrument, which is an important feature when using the instrument for treatment.

The material may be of a type that changes color upon heating, or perhaps changes from a gel-state to a solid-state, or vice versa in the case of e.g., wax. If such a material is used, then the calorimeter calculations may also include an additional term that allows for the specific heat capacity and mass of the material indicator to be accounted for. If the material is thin or lightweight in comparison to the mass of the calorimeter liquid, then it may not be necessary to account for the heating of the additional material indicator.

The heat sensitive load material may be formed as a cylinder into which the instrument tip can be inserted such that a sleeve of the heat sensitive load material is arranged around the instrument tip.

Instead of liquid, a powder (or granular material) may be used as an absorption material. The particle size and/or the shape of the particles may be such that the powder can be stirred, for example by using the stirrer and/or by rotating the calorimeter cell. In other words, the powder may have flow properties similar or comparable to the ones of liquid. Material examples for the powder are iron ferrite, conductive carbon black, graphite, carbonyl iron, and/or carbon nanotubes. The average particle size may be between 100 nm and 780 nm, optionally 100 nm, 240 nm, 400 nm, or 780 nm. In general, the average particle size may be chosen to be adapted to the wavelength of the electromagnetic radiation emitted by the electrosurgical instrument. Optionally, the powder is a mixture of individual ingredients which may be varied to achieve a preferred load impedance. A non-lossy, radio-transparent material, such as ceramic or plastic may also be introduced to hold the particles as a solid in order to obtain a specified impedance or material shaping.

The absorption material in form of solid may include a material socket for receiving the instrument tip. For example, a plurality of solids is provided wherein each solid is formed to be received in the cell container but includes a socket of a different size and/or shape for receiving different types of electrosurgical instruments. If the absorption material is a solid, a stirrer is not provided. A plurality of temperature sensors may be provided to accurately measure the temperature change or, optionally, the temperature profile/distribution/gradient within the solid absorption material. The measured temperature gradient can be used to model/calculate/determine the electromagnetic energy or power received by the solid. In this embodiment, the at least one temperature sensor may be arranged within the solid absorption material for increasing the accuracy of the measurement of the temperature distribution within the solid. To this end, the solid absorption material may include a connector to connect the temperature sensors to the controller. The solid absorption material may include a Radiation Absorptive Material (RAM) such as is used in microwave attenuators and microwave anechoic chambers (e.g. homogeneous mixes of iron ferrite, conductive carbon black, graphite, carbonyl iron, and/or carbon nanotubes) and/or meta materials.

In an optional embodiment, the absorption material includes a meta material and at least one absorber, wherein the meta material is configured to guide the electromagnetic radiation to the at least one absorber and the at least one absorber is configured to absorb the electromagnetic radiation.

Meta material structures, for example, using periodic structures or split-ring resonators, may be used to guide or focus electromagnetic radiation onto the smaller, thermal absorber, reducing its mass and thus beneficially increasing its temperature for a given power output and speeding up the time required to make a measurement. A further benefit is that a metamaterial structure may be fabricated so as to avoid the necessity of close contact of the instrument with the solid absorber which may be beneficial to maintaining a sterile environment.

The absorber may be made from the same material as described in conjunction with the solid absorption material. The mass and/or the volume of the one or more absorber is smaller than the mass and/or volume of the metamaterial. The absorber may be arranged within the meta material. The outer shape of the metamaterial may be formed to be inserted into the cell container. The meta material may include a socket for receiving the instrument tip. Due to the provision of the meta material, the socket may not be specifically adapted to a particular type of instrument tip. Rather, the socket may have a shape and dimensions configured to receive a plurality of different instrument tips. That is, the socket may be larger than the instrument tip such that when the instrument tip is within the socket the outer surface of the instrument tip is spaced from the inner surface of the socket by at least 1 mm, for example, at least 2 mm or 5 mm.

The at least one temperature sensor may be arranged within or close to the at least one absorber. In this way, the temperature sensor can accurately measure the temperature change in the absorber.

Optionally, the absorption material includes a gas and/or a plasma which may be ignited (e.g. struck) and/or maintained (e.g. sustained) by the electromagnetic radiation emitted by the electrosurgical instrument. The lid may be configured to seal the calorimeter cell in a gas-tight manner.

The invention also refers to an assembly comprising the electrosurgical instrument calorimeter as described above and the electrosurgical apparatus as described above.

A method for measuring an electromagnetic energy and/or power output of an electrosurgical instrument powered by a generator comprises the following steps: a) filing a predetermined amount of an absorption material in a calorimeter cell of an electrosurgical instrument calorimeter; b) placing the electrosurgical instrument in such a position that (e.g. a majority of the, or an entirety of the, or a substantial portion of the) electromagnetic radiation emitted by the electrosurgical instrument is absorbed (e.g. completely absorbed) by the absorption material; c) operating the electrosurgical instrument for a predetermined time span to emit electromagnetic radiation into the absorption material; d) measuring a temperature change of the absorption material; and e) calculating an energy and/or power of the electric magnetic radiation emitted by the electrosurgical instrument based on the measurement temperature change, the amount of liquid in the calorimeter cell, and/or the time span during which the electromagnetic radiation is generated.

The method described above may be used in conjunction with the electrosurgical instrument calorimeter described above. In particular, the characteristics, features, and/or advantageous effects described in conjunction with the electrosurgical instrument calorimeter may equally apply to the method for measuring an electromagnetic power output of an electrosurgical instrument.

As described above, the calculation of the electromagnetic the power output of the electrosurgical instrument is based on three main parameters: the detected temperature change induced by the absorption of the electromagnetic radiation by the liquid (this is measured using the at least one temperature sensor), the amount of liquid within the calorimeter cell (this may be determined by providing a certain amount of the liquid and/or by weighing the amount of liquid that is field into the calorimeter cell), and the time span in which the electromagnetic radiation is generated and emitted by the electrosurgical instrument (this parameter may be set with the generator). The calculation based on these three main parameters assumes that the energy loss of the liquid (e.g., a cooling of the liquid) occurs on a significantly longer time period compared to the heating of the liquid and that the complete power that is emitted by the electrosurgical instrument is completely absorbed by the liquid.

Some of these parameters may be valid for short time spans of the calorie calorimeter measurements (e.g. energy losses by cooling may be insignificant over short periods of time). Other parameters may be adjusted for by calibrating the calorie measurements.

In an optional embodiment, step b) includes inserting an instrument tip into a depth gauge socket, attaching a depth gauge clamped electrosurgical instrument such that the depth gauge clamp is in contact with an opening at a depth gauge socket, closing the calorimeter cell with a lid, and inserting the instrument tip into a passageway of the lead until the depth gauge clamped abuts against the lid.

Step b) may further include holding the electrosurgical instrument in a fixed relationship with respect to the calorimeter cell using a support structure.

In an optional embodiment, step b) includes placing an energy output port of a waveguide of the electrosurgical instrument above or close to the liquid.

This step may be executed if the electrosurgical instrument includes a waveguide, whereby the energy output port is arranged directly above or at the liquid.

Step c) may be executed only after the temperature of the liquid reaches a substantially equilibrium temperature, wherein optionally the temperature changes recorded with respect to the substantially equilibrium temperature.

The equilibrium temperature preferably is that temperature to which the liquid settles after as a prolonged time period. For example, the equilibrium temperature corresponds to the temperature of the surroundings assuming that the ambient air temperature is constant.

The substantially equilibrium temperature may be considered to be reached if the standard deviation of the previously recorded temperatures is below a predetermined threshold. Alternatively or additionally, it is determined that the liquid has reached the substantially equilibrium temperature if the difference between the liquid temperature and the ambient air temperature is below a certain threshold.

The temperature of the liquid may be changed upon inserting the stirrer or the electrosurgical instrument. Furthermore, the temperature of the liquid may not have reached the substantially equilibrium temperature if a sufficient amount of time has passed after the previous calorimeter measurement. The determination of the substantially equilibrium temperature may be replaced by a control with which a calorimeter measurement may only be performed after a predetermined amount of time has passed after the insertion of the electrosurgical instrument into the liquid or a previous calorimeter measurement.

In optional embodiment, the method further comprises the step of stirring the liquid in the calorimeter cell. To this end, the above-described stirrer may be used.

In a further optional embodiment, steps c) and d) are automatically executed after receiving a start signal, wherein optionally a controller of the electrosurgical instrument calorimeter and the generator are connected to each other, wherein further optionally the start signal is generated by an external user interface that is connected to the controller and/or the generator or by an automated test equipment Systems that is connected to the controller and/or the generator.

Alternatively, step d) is used to detect the execution of step c). In this embodiment, the detection of a change in the temperature of the liquid that is faster than a change in temperature due to heat loss is used to determine that the electrosurgical instrument has emitted electromagnetic radiation into the liquid. In this embodiment, a connection between the control and the generator does not need to be provided since the controller is capable of determining the actuation of the electrosurgical instrument.

In optional embodiment, the presence of electromagnetic radiation within the calorimeter cell is detected, wherein optionally the execution of steps c), d) and/or e) is stopped or prohibited if an intensity of the detected electromagnetic radiation is above a predetermined threshold. To this end, the radiation detector as described above may be used.

In optional embodiment, the calculation of step e) is further based on a temperature of the surrounding of the electrosurgical instrument calorimeter, the energy introduced by a stirrer stirring the liquid into the liquid, and/or the heat absorption of the electrosurgical instrument.

In optional embodiment, a heat sensitive load material is placed around the instrument tip of the electrosurgical instrument, electrosurgical instrument is operated or steps b) and c) are executed, and a radiation pattern of the instrument tip of the electrosurgical instrument as identified by a local change of the physical property of the heat sensitive load material induced by the irradiation of electromagnetic radiation emitted by the instrument tip.

The heat sensitive load material may be attached to the instrument tip prior to the calorimetry measurement. The heat sensitive load material is used to obtain information about the radiation pattern of the instrument tip. This cannot be determined using the calorimeter measurements which is capable of determining the overall energy absorbed by the liquid, i.e. emitted by the electrosurgical instrument. On the other hand, the heat sensitive load material cannot be used to determine the overall energy or power emitted by the instrument tip. Thus, the heat sensitive load material and the electrosurgical instrument calorimeter are complimentary measurement tools.

The calculation step e) may be further based on a specific heat capacity of the heat sensitive load material and/or the mass of the heat sensitive load material.

These parameters may be used to determine how much energy is absorbed by the heat sensitive load material and, thus, does not contribute to the heating of the liquid. This aspect is particularly relevant if the temperature change of the liquid is recorded only over a short period of time such that an equilibrium between the heat of the heat sensitive load material and the liquid cannot be reached. However, if the mass of the heat sensitive load material is low, this aspect may be neglected.

It is also possible to include the mass and specific heat capacity of the instrument tip immersed into the liquid in the calculation of the energy/power output of the electrosurgical instrument. The electrosurgical instrument itself receives heat which effectively cools the liquid. Thus, by considering the amount of heat the electrosurgical instrument absorbs, the calorimetry measurement can be made more accurate.

BRIEF DESCRIPTION OF THE DRAWINGS

Embodiments of the invention will now be described by way of example with reference to the accompanying drawings in which.

DETAILED DESCRIPTION; FURTHER OPTIONS AND PREFERENCES

Figure 1:
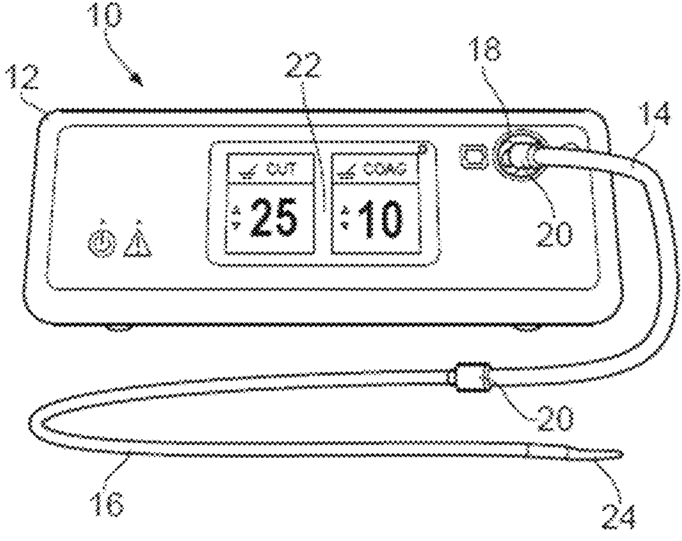
FIG. 1 shows a perspective view of an electrosurgical apparatus.

FIG. 1 shows a perspective view of an electrosurgical apparatus 10 which includes a generator 12, a cable 14, and an electrosurgical instrument 16. The generator 12 is configured to generate an alternating (AC) voltage in the radio frequency range and/or the microwave range. The AC voltage is present at a generator output 18 to which the cable 14 can be connected to using a cable connector 20. The generator 12 further includes a generator interface 22 with which the frequency and/or the amplitude of the generated voltage can be set. The generator interface 22 may be a touch screen. The voltage can be generated as a continuous wave (CW) or in bursts of short pulses for periods up to a few minutes.

The electrosurgical instrument 16 may be configured as a scoping device that can be inserted into a body cavity. The electrical surgical instrument 16 depicted in FIG. 1 may have an instrument tip 24 which is advanced to the target site within the body. The instrument tip 24 is configured to emit electromagnetic radiation. In other words, the instrument tip 24 emits electromagnetic radiation which corresponds to the voltage generated by the generator 12. The instrument tip 24 may include a monopole antenna and/or a dipole antenna. The electromagnetic radiation emitted by the instrument tip 24 is used for ablation/coagulation or cutting (resecting or distracting) of tissue at the target site within the body.

The cable 14 may be a coaxial cable and is provided for connecting the electrosurgical instrument 16 to the generator 12. To this end, the cable connectors 20 may be used for connecting the cable 14 to the electrosurgical instrument 16 and/or to the generator 12. The cable 14 is configured to transmit the AC voltage/current generated by the generator 12. In other words, the cable 14 is configured to transmit AC currents having frequencies in the radio frequency range and/or the microwave frequency range.

Figure 2:
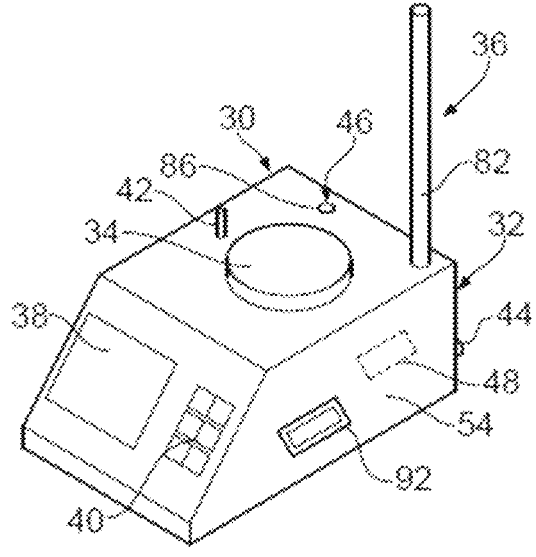
FIG. 2 shows a perspective view of an electrosurgical instrument calorimeter.

The electrosurgical instrument calorimeter 30 depicted in FIG. 2 includes a calorimeter base 32, a calorimeter cell 34, and a support structure 36. Optionally, the electrosurgical instrument calorimeter 30 includes a display 38, a user interface 40, a motor 42, a control connector 44, a depth gauge mechanism 46, a controller 48, a stirrer 50, and/or a lid 52.

The calorimeter base 32 may include a housing 54 and include further components for supporting the various parts of the electrosurgical instrument calorimeter 30. The calorimeter base 32 may be configured to be arranged on a table or a flat surface. The housing 54 of the calorimeter may be of a standard construction employed in laboratory instruments, for example, folded sheet metal with moulded plastic fascia and panels. The housing 54 may house all the components of the electrosurgical instrument calorimeter 30 listed below.

Figure 4:
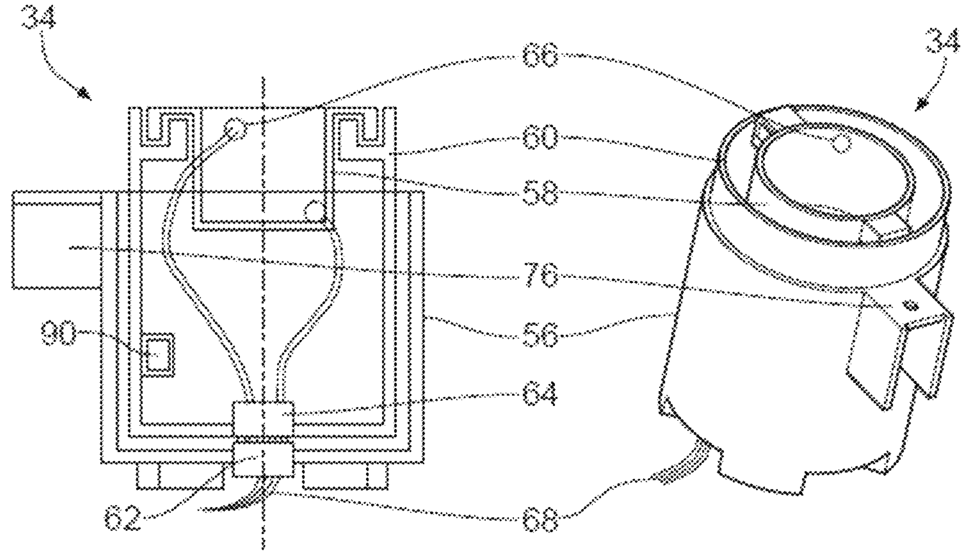
FIG. 4 shows a cross-sectional view (left) and a perspective view of a calorimeter cell of the electrosurgical instrument calorimeter.

The calorimeter cell 34 may include three concentric component parts as shown in FIG. 4, although any or all the parts could be combined into a single part as necessary: an (outer) cell housing 56, an (inner) cell container 58, and a removable attachment 60 that is used to mechanically secure the smaller cell container 58 inside the larger cell housing 56 for ease of access.

The cell housing 56 may be permanently attached to the calorimeter base 32 and/or to the housing 54 and acts as a receptacle for holding the attachment 60 that contains the cell container 58. It may also contain a first connector 62 for making contact with a mating second connector 64 on the attachment 60 for at least one temperature sensor 66.

The cell container 58 may sit permanently inside the top of the attachment 60 and holds a known, fixed mass of an absorption material 110 which will be heated by the electrosurgical instrument 16. The absorption material 110 may be a liquid, a powder of solid particles (e.g. granular material), a solid, a gas and/or a plasma. In the following, the description of the embodiments of the invention relate to liquid as an example of the absorption material 110. However, the invention is not limited thereto. A powder of solid particles, a solid, a gas and/or a plasma may be used instead of a liquid.

The cell container 58 may have a low mass to reduce the amount of thermal energy absorbed from the liquid. It also is waterproof and be able to insulate the liquid, reducing the amount of thermal energy dissipated into the surroundings by radiation. A vacuum-flask arrangement could equally be used but a mechanically thin plastic insulating material is preferred due to its durability, low thermal mass, and rigidity.

The cell container 58 includes an arrangement of the at least one temperature sensors 66 (see FIGS. 5 and 6) which can include miniature thermistors or other thermal transducers that are used to provide a diversity of temperature measurements of the liquid at dissimilar locations. For example, locating separate temperature sensors 66 at opposite ends of the cell container 58 will allow the electrosurgical instrument calorimeter 30 to identify whether the liquid is sufficiently mixed to prevent pockets of heat from forming that might affect the accuracy of the overall power measurement. Note that further temperature sensors may also be placed within or without of the calorimeter base 32 or attachment to measure and account for ambient air temperature that might also contribute to the overall measurement accuracy (which will be describe later). It is also possible to use a single temperature sensor 66.

The removable attachment 60 or carrier is used to provide mechanical support and to hold the lightweight cell container 58 and its temperature sensor connections 68. In this way the attachment 60 allows the simple removal (from the calorimeter base 32) of the cell container 58 and its contents without the necessity to be cautious when handling the potentially fragile cell container 58 and its temperature sensor connections 68. At the bottom of the attachment 60 is the second connector 64 which connects the temperature sensor 66 to controller 48 in the calorimeter base 32 via the mating first connector 62 in the cell housing 56. These may be spring-form or other easy-mating connectors for convenience of operation.

The attachment 60 may additionally be insulated, made of an insulating material, or contain a thermal reflector such as aluminium foil or aluminised plastic to keep as much heat within the calorimeter cell 34 as possible.

Figures 5, 6, 7:
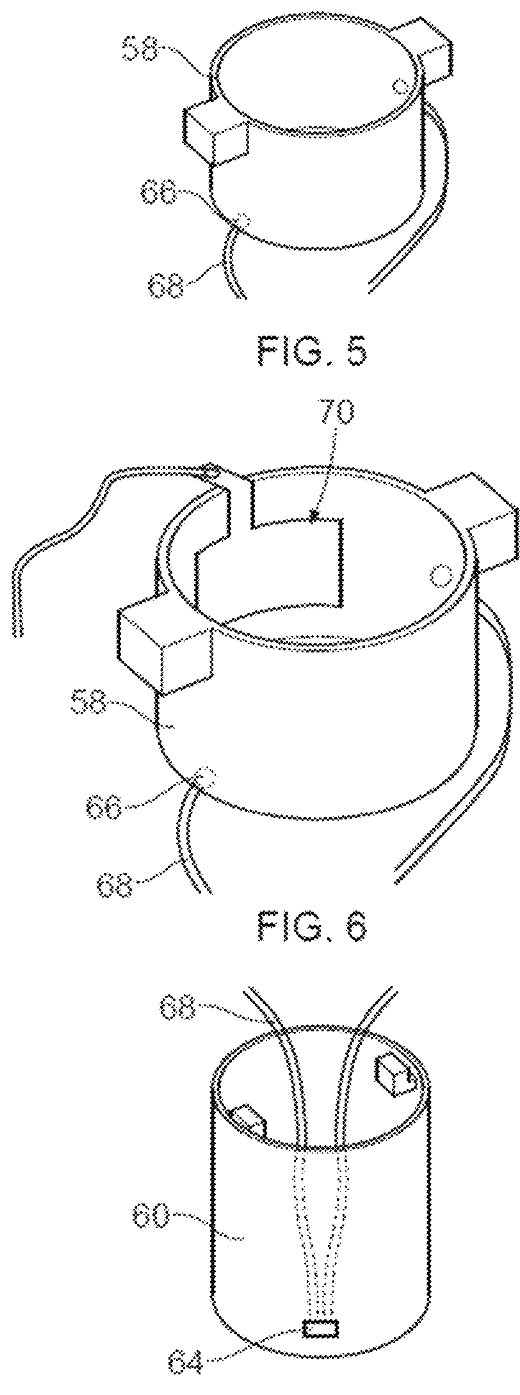
FIG. 5 shows a perspective view of a cell container of the calorimeter cell.
FIG. 6 shows a perspective view of another embodiment of the cell container of the calorimeter cell.
FIG. 7 shows a perspective view of an attachment of the calorimeter cell.

As visible in FIG. 7, the attachment 60 for cell container 58 may include temperature sensor connections 68 such as one or more wires and the second connector 64 mating with the first connector 62 of the cell housing 62.

Of necessity, some surgical operations require the delivery of low quantities of energy into tissue while other operations use larger electrosurgical instruments 16 to deliver high quantities of energy into tissue. Use of the attachment 60 to carry the cell container 58 and a standardised interface of the second connector 64 facilitates the use of a variety of liquid volumes that may be tailored to suit a range of electrosurgical instruments 16. Low volumes of liquid may be used for low energy measurements and larger volumes of liquid for high energy measurements.

The electrosurgical instrument calorimeter 30 may be used, equally, with bipolar electrosurgical instruments 16 and monopolar electrosurgical instruments 16. With bipolar electrosurgical instruments 16, the electrical return path or electromagnetic counterpoise is normally the outer shield of a connecting coaxial cable 14 or a separate electrode within the instrument tip 24. For monopolar operation, a return electrode 70 is placed inside the calorimeter cell 34 (in particular the cell container 58) to make conductive contact between the liquid and the instrument tip 24, as shown in FIG. 6. Bipolar electrosurgical instruments 16 may also be used in monopolar mode along if the monopolar return electrode 70 is connected in circuit. The return electrode 70 may be constructed from thin foil, such as copper, silver, or gold, or deposited onto the surface of the cell container 58 as a conductive coating.

In normal operation at microwave frequencies, the liquid type to be inserted into the cell container 58 may be water of an appropriate purity. The choice of liquid is not limited to any one type but should be of a type that is similar to the impedance of the tissue with which that the electrosurgical instrument 16 is normally used. If an electrosurgical instrument 16 that delivers infra-red energy is used, then it may be appropriate to fill the cell container 58 with a suitable infra-red absorbing substance, rather than pure water that allows a high degree of transmission of infra-red light. Similarly, if the electrosurgical instrument 16 is to deliver low-frequency RF power of around 400 kHz, then it may be appropriate to use a saline solution that is electrically conductive. Not all electrosurgical instruments 16 and power frequencies may be suited to use the same, single cell container 58 and the use of the attachment 60 facilitates the use of a range of suitable cell containers 58 and appropriate liquids.

The stirrer 50 disperses the heat from the instrument tip 24 around the liquid inside the cell container 58, preventing heat pockets from forming. The stirrer 50 may mix the liquid both vertically and horizontally as well as have a low mass so as to reduce the amount of thermal energy it takes from the liquid, and a speed that is low enough that the frictional energy imparted to the liquid is insignificant compared with the energy to be measured. Through software and/or calibration, the electrosurgical instrument calorimeter 30 may be able to calibrate and subtract the mechanical frictional energy component that is imparted to the liquid from the final power and energy results, making the overall measurement more accurate.

Figure 8:
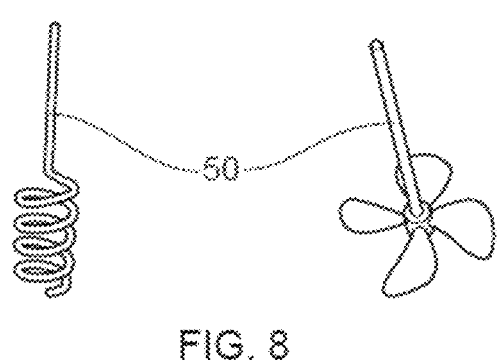
FIG. 8 shows perspective views of two embodiments of stirrers of the electrosurgical instrument calorimeter.

Typical stirrer types are shown in FIG. 8, a first type (depicted left) being a stiff helical wire and a second type (depicted right) being a miniature impeller, such as might be found on model boats. Other types might include but are not limited to magnetically coupled or ultrasonic stirrers. With the goal of minimising overall thermal mass and the frictional movement energy imparted to the liquid the preferred embodiment of the invention may use a simple lightweight mechanical stirrer, as shown.

Figure 9:
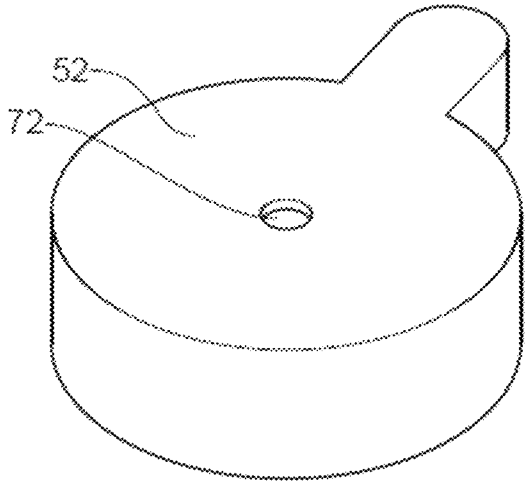
FIG. 9 shows a perspective top view of a lid of the electrosurgical instrument calorimeter.
Figure 10:
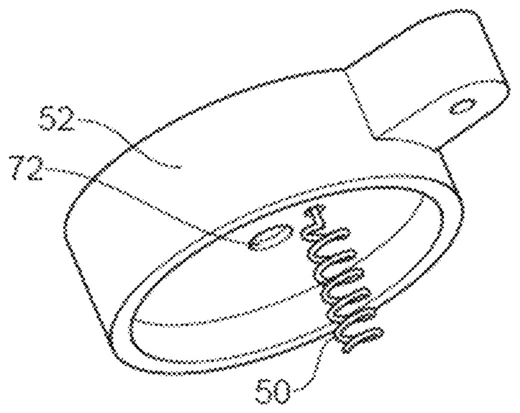
FIG. 10 shows a perspective bottom view of the lid of FIG. 9.

The lid 52 is detachable or movable and an embodiment thereof is shown in FIGS. 9 and 10. The lid 52 sits on top of the cell housing 56 and contains a transmission device (not shown in FIGS. 9 and 10) which may include gears, cogs and/or belt drive components for the motor 42 to spin the stirrer 50. The stirrer 50 is rotatably attached to the lid 52.

The lid 52 may be hollow inside, creating an air pocket to help insulate the cell container 58. The bottom of the lid 52 may act as the top of the cell container 58.

The lid 52 may include a passageway 72 through which the electrosurgical instrument 16 can be inserted into the liquid. In the passageway 72 there may be a grommet to help holding the electrosurgical instrument 16 and also to reduce loss of thermal energy through the passageway 72. A depth gauge clamp 74 to be described later may sit on top of the lid 52 to hold the electrosurgical instrument 16 at the correct depth through the passageway 72. A recess or other elements of the lid 52 may hold-fast the depth gauge clamp 74.

The motor 42 is an electrical motor which may be attached to a motor bracket 76 fixed to the cell housing 56. The motor 42 is arranged within the housing 54 and, thus, not visible in FIGS. 2 and 3. Only a motor axle of the motor 42 protrudes from the housing 54. The motor axle attaches to the lid 52 which may have a cog and/or belt-drive system that will turn the stirrer 50 which stirs the liquid.

An alternative location for the motor 42 might be on the lid 52 itself, although the preferred embodiment is where the motor 42 is located to one side so that no electrical connections are brought outside of the housing 54.

The motor's speed may be switched or varied to affect an appropriate mixing speed, by current limiting, by shaft rotational sensing, and/or by precisely stepped angular control. This control may be executed by the controller 48 to which the motor 42 may be electronically connected.

The display 38 may include, for example, a 20-by-4 character alphanumeric or graphical display and display the operational parameters of the electrosurgical instrument calorimeter 30, the results of any measurements, and/or brief instructions on how to operate the apparatus.

At the back of the housing 54, there may be one or more control connectors 44 allowing the electrosurgical instrument calorimeter 30 to be linked to external electronic devices, such as the generator 12. Various control modes may be executed whereby: the electrosurgical instrument calorimeter 30 (in particular the controller 48) controls the generator 12, or for the generator 12 to control and trigger the calorimeter measurement process. Alternatively or additionally, an external user interface 78, such as a foot pedal system as is commonly used in electrosurgical systems, may be attached to the generator 12 or the control connector 44 in order generate a start signal for starting the calorimetry measurement. The control connector 44 may by connected to an automated test equipment system 80 which allows full or partial remote control of the electrosurgical instrument calorimeter 30 and/or the generator 12. The automated test equipment system 80 may include a server and/or computer which contain a software for provide for automated calorimetry measurements.

An important aspect of providing flexible control options is to allow for the microwave power from the generator 12 to be turned on by the electrosurgical instrument calorimeter 30 rather than being operated by a user, thus reducing human error in the timing of measurements. A range of control options are discussed further below. The control connector 44 may be connected to the controller 48 via wires which extend within the housing 54.

The user interface 40 may comprise one or more user command keys which can be provided on the front fascia alongside the display 38. The user interface 40 allows a user to configure and control all parameters of the calorimeter operation. The user interface 40 may optionally be incorporated into a touch-sensitive screen for aesthetic or operational needs.

The calorimeter base 32 may include the controller 48 which can comprise a microcontroller and electronic circuitry (not shown in diagrams) that, through software, controls one, several or all aspects of calorimeter operation, including but not limited to: configuring operational parameters, timing of power delivery and sequencing of temperature measurements, acting on user interface commands, acting on and producing control events from and to the control connectors 44, controlling the timing and speed of the motor 42 and converting the formats of all information to be displayed or conveyed to the user. The controller 48 is arranged within the housing 54 and, thus, not visible from the outside (see broken lines in FIGS. 2 and 3).

The support structure 36 may include a stand 82 and an instrument guide clamp 84. The support structure 36, in particular the stand 82, may be attached to the calorimeter base 32. However, the support structure 36 may be component separate to the calorimeter base 32.

The stand 82 can include a rod-like or other support structure that helps to hold the electrosurgical instrument 16, and which may also be clamped to the calorimeter base 32 for security. The instrument guide clamp 84 can be attached close to the top of the stand 82. The stand 82 provides both vertical and lateral stability to the electrosurgical instrument 16 and instrument guide clamp 84.

Figure 3:
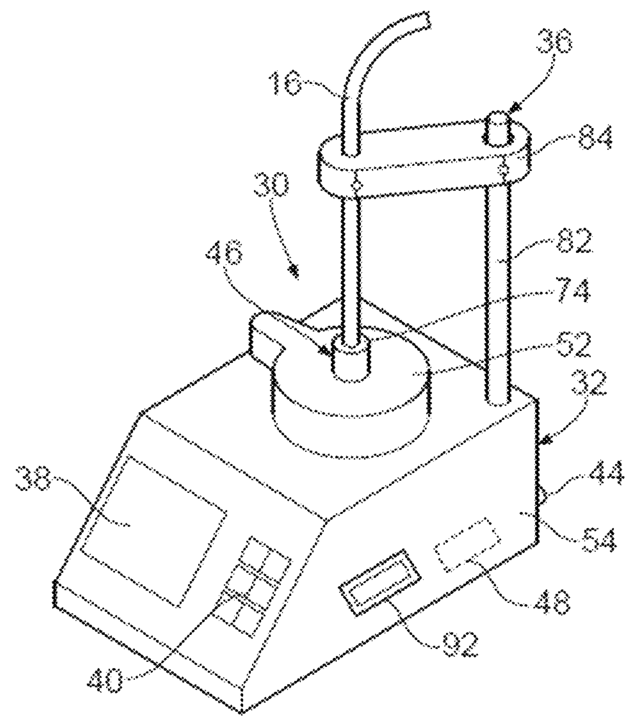
FIG. 3 shows a perspective view of the electrosurgical instrument calorimeter of FIG. 2 in combination with an electrosurgical instrument of the electrosurgical apparatus of FIG. 1.

The instrument guide clamp 84 in combination with the stand 82 holds the electrosurgical instrument 16 upright, centrally, and laterally located in the liquid inside the calorimeter cell 34, as shown in FIG. 3. The optional depth gauge clamp 74 and/or a further clamp mechanism for the electrosurgical instrument 16 itself, within the passageway 72, may provide additional stability if required depending on the type of electrosurgical instrument 16 in use. There may also be variations on the structure of the instrument guide clamp 84 to accommodate a range of instruments. For example, laparoscopic instruments are shorter, of thicker diameter (5 mm), and have a rigid shaft compared to endoscopic instruments (2 mm diameter). The instrument guide clamp 84 and the stand 82 may be adjusted to freely swing the electrosurgical instrument 16 to multiple locations on or off the calorimeter base 32, for example, the electrosurgical instrument 16 may first be aligned for correct depth of operation using the depth gauge mechanism 46.

Figure 11:
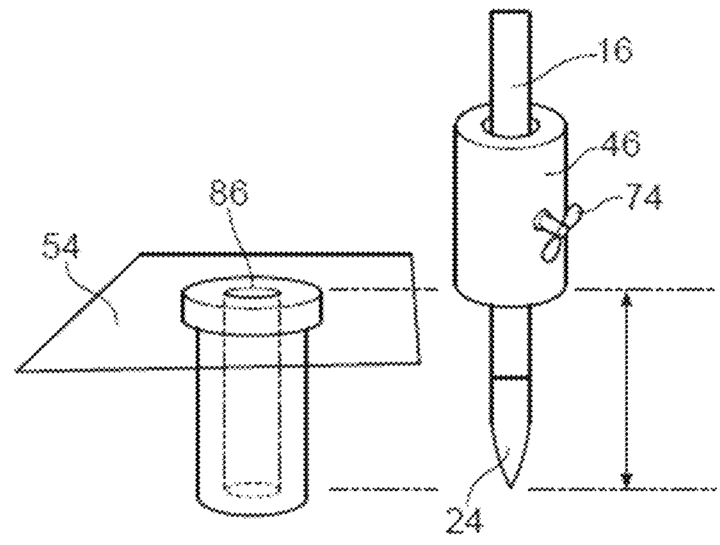
FIG. 11 shows a perspective view of a depth gauge socket (left) and a depth gauge clamp attached to the electrosurgical instrument (right)

The depth gauge mechanism 46 may be provided on the calorimeter base 32 (in particular on the housing 54) to facilitate the correct (repeatably consistent) vertical placement of the instrument tip 24 inside the cell container 58 and, thus, in the liquid. The correct positioning is important to maintain repeatability and ensure that no electromagnetic radiation from the instrument top 24 escapes the calorimeter cell 34. The preferred implementation is to use a two-part mechanism, as shown in FIG. 11.

A first part of the depth gauge mechanism 46 is a calibrated depth gauge socket 86 in the housing 54 that temporarily accepts the instrument tip 24 and includes a depth to match the distance from the top of the lid 52 to the centre of the cell container 58, prior to usage.

A second part of the depth gauge mechanism 46 is the depth gauge clamp 74 which may be a collar, clamp or cylinder that fits around the electrosurgical instrument 16 and is adjusted so that, when clamped, the instrument tip 24 protrudes from its base by the depth of the aforementioned depth gauge socket 86. This ensures a consistent depth of operation in the liquid. A tightening mechanism may be attached to the depth gauge clamp 74 to ensure that it does not slip during use. FIG. 11 depicted the depth gauge socket 86 attached to housing 54 and the depth gauge clamp 74 attached to electrosurgical instrument 16.

Figure 12:
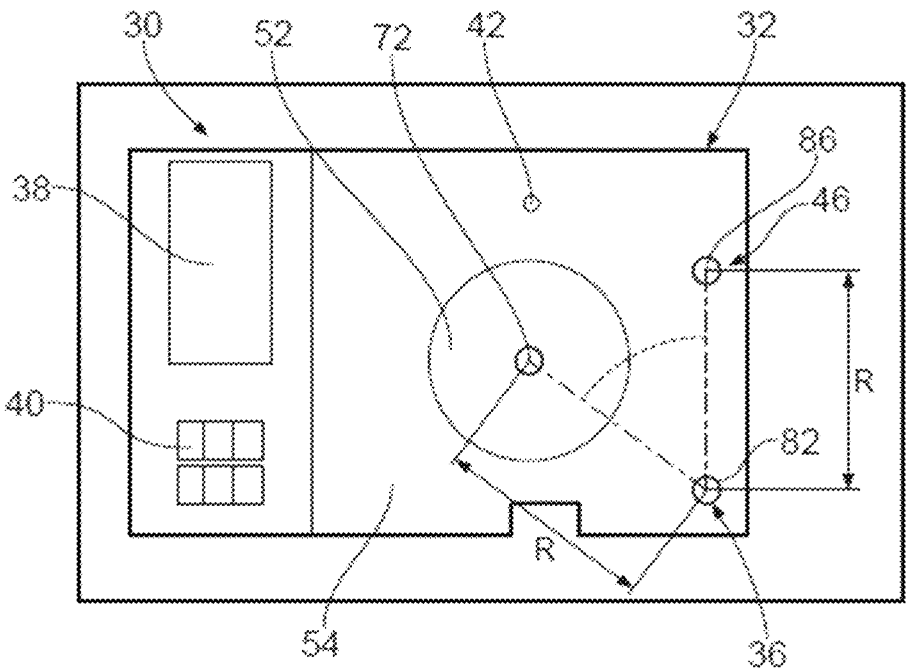
FIG. 12 shows a top view of the electrosurgical instrument calorimeter.

Furthermore, the depth gauge socket 86 may at the same radius away from the stand 82 as the centre of the cell container 58 so the stand 82 can be twisted back and forth above the passageway 72 and the depth gauge socket 86, as shown in FIG. 12.

Alternative depth gauge mechanisms 46 might, instead, be used, for example where a single part system is employed, such as: creating a platform within the cell container 58, or by a fully or partly automated method of robotic instrument placement, or by an optical or ultrasonic sensor.

A further alternative depth gauge mechanism 46 may be incorporated into a tightening mechanism within the instrument guide clamp 84 and the stand 82, meaning that a separate instrument depth gauge clamp 74 is not required.

A variation on the depth gauge mechanism 46 is for it to be removable, for cleaning, or exchangeable for a disposable unit in order to preserve a sterile environment.

The electrosurgical instrument calorimeter 30 may be powered from an AC-mains to low-voltage power converter in order to keep liquid parts of the electrosurgical instrument calorimeter 30 a safe distance away from mains electricity. For example, a 240V AC to 9V DC power adapter may be used.

An option of including an internal rechargeable battery is considered which would sit inside the electrosurgical instrument calorimeter 30 (in particular, inside the housing 54) and will increase the distance of the liquid to a mains supply. It will also allow for the device to be more mobile. If powered by a battery, the electrosurgical instrument calorimeter 30 may include an automatic power-off function that detects a period of inactivity and turns itself off to preserve battery power.

The electrosurgical instrument calorimeter 30 may be connected to operate in a number of flexible modes that offer benefits to obtaining a range of measurement types.

Figure 13:
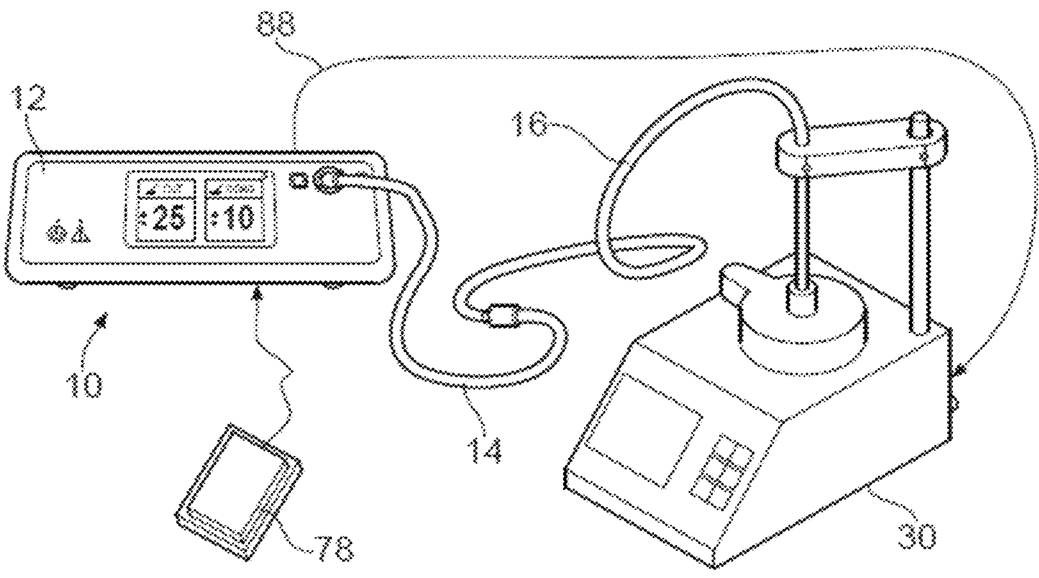
FIG. 13 shows a perspective view of the electrosurgical apparatus, the electrosurgical instrument calorimeter, an external user interface, and a signal cable.

FIG. 13 depicts a situation in which the electrosurgical instrument calorimeter 30 is triggered by the generator 12. A signal cable 88 is connected from the generator 12 to the electrosurgical instrument calorimeter 30 (in particular, to the control connector 44). In addition, the external user interface 78 is connected to the generator 12. In this mode the generator 12 may send an appropriate trigger signal to the electrosurgical instrument calorimeter 30 to start and stop the measurement process in response to user commands (start signal) from the external user interface 78. This mode of measurement is particularly useful to mimic the conditions experienced during surgery.

Figure 14:
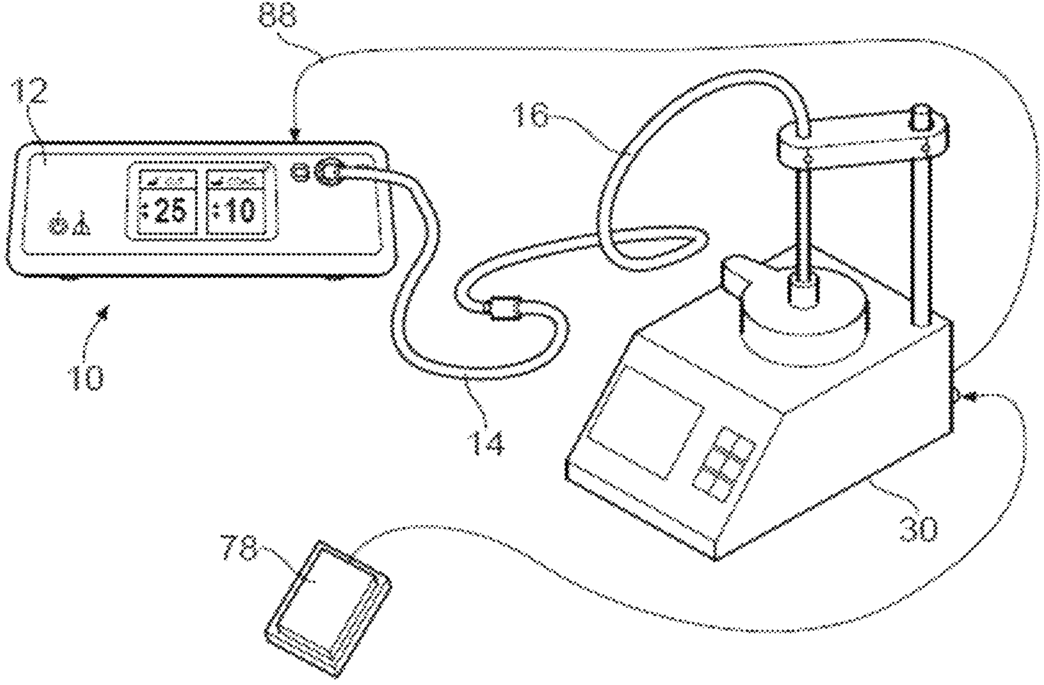
FIG. 14 shows a perspective view of the electrosurgical apparatus, the electrosurgical instrument calorimeter, the external user interface, and the signal cable in a second connection arrangement.

In FIG. 14 the signal cable 88 is connected from the electrosurgical instrument calorimeter 30 to the generator 12 and the external user interface 78 to the electrosurgical instrument calorimeter 30. In this mode the electrosurgical instrument calorimeter 30 may send a trigger signal to the generator 12 to start and stop the power delivery process in response to user commands from the external user interface 78. This mode of connection may be useful to measure response times of the power delivery. The generator 12 may also be triggered from the user interface 40 of the electrosurgical instrument calorimeter 30, without use of the external user interface 78.

Figure 15:
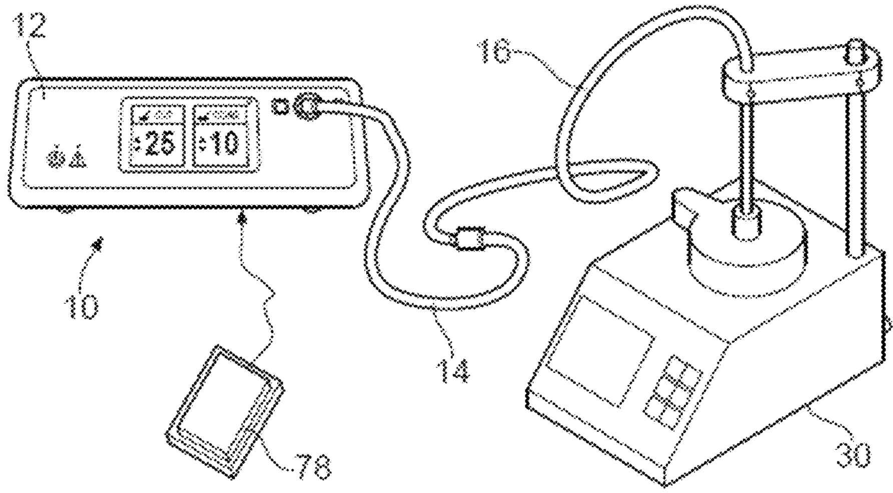
FIG. 15 shows a perspective view of the electrosurgical apparatus, the electrosurgical instrument calorimeter, and the external user interface in a third connection arrangement.

In FIG. 15 the electrosurgical instrument calorimeter 30 and generator 12 are not connected by any signal cable 88 at all. A feature of the electrosurgical instrument calorimeter 30, here, is that the controller 48 may be programmed to detect and respond to a sharp temperature increase compared to the average temperature level (or a substantially equilibrium temperature) and statistical variance. This automatic-detection mode of operation is particularly useful for simplicity of use.

Figure 16:
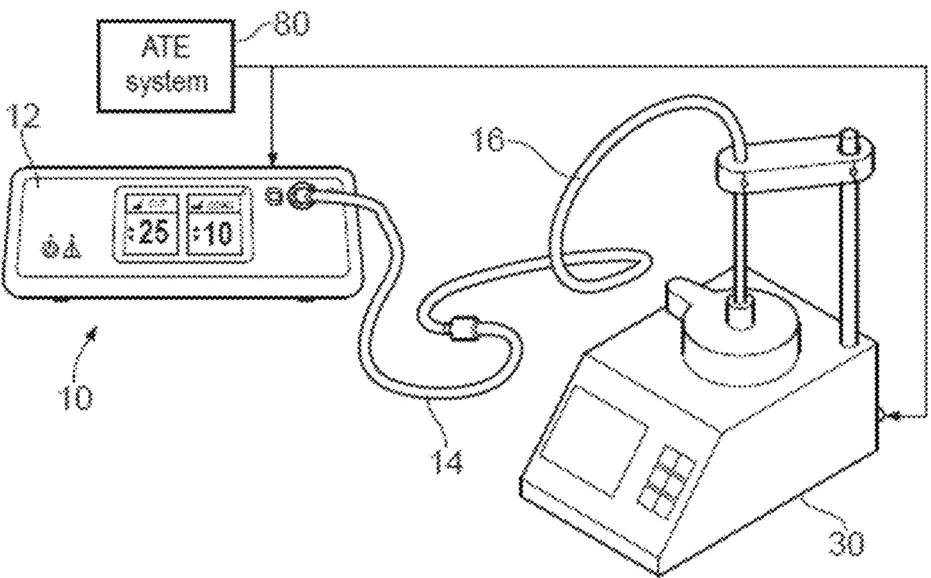
FIG. 16 shows a perspective view of the electrosurgical apparatus, the electrosurgical instrument calorimeter, and an automated test equipment system.

In FIG. 16 the generator 12 and the electrosurgical instrument calorimeter 30 may be connected into the automated test equipment (ATE) system 80, for example by wired Ethernet, Wi-Fi, Bluetooth, USB, or serial connection that supports a communication protocol. The protocol may be, for example, General Purpose Interface Bus (GPIB) or the Standard Commands for Programmable Instruments (SCPI), as are in common use, or a proprietary protocol such as the Creo Medical Kamaptive™ protocol.

This mode of operation facilitates unattended, programmed measurements that can be used for assessing reliability and repeatability, for example in validation and verification studies.

In an optional embodiment of the invention, the parameters of the electrosurgical instrument calorimeter 30 may be input using a self-provisioning system, for example using a code number that is entered by the user, or by a scanner, such as a radiofrequency identification (RFID) or optical barcode scanner that is able to identify the attached electrosurgical instrument 16. This kind of automatic operation is beneficial to reduce human-induced errors, particularly for validation and verification exercises.

The electrosurgical instrument calorimeter 30 may also be equipped, for example, inside the calorimeter cell 34, with an electromagnetic radiation detector 90. Any detection of high levels of electromagnetic radiation by the radiation detector 90 may alert the user and shut down the power delivery (if connected appropriately). The accuracy of the electrosurgical instrument calorimeter 30 relies on largely 100% absorption into the liquid of power from the instrument tip 24 and any power not being absorbed should be considered as producing inaccurate results.

A method the electromagnetic power output of the electrosurgical instrument 30 will be described:

Firstly, the cell container 58 is filled to the correct depth or mass of liquid. This may be accomplished in a number of ways, for example by weighing the liquid as it is poured into the detached cell container 58 and attachment 60, or by filling to a level marked on the cell container 58 itself. In an advanced embodiment, a self-filling valve and inlet/outlet system may be fitted to allow the electrosurgical instrument calorimeter 30 to replenish its liquid supply from an external source. In another advanced embodiment, an electronic or mechanical force gauge may be incorporated into the components of calorimeter cell 34 in order to measure the weight of liquid added.

In the embodiment described above, without advanced features, the user may simply enter the mass of liquid and type of liquid into the configuration parameters on the user interface 40, or by network connection commands.

The user may now introduce the filled cell container 58 and attachment 60 into the cell housing 56 and secure the lid 52 and transmission device on top of the calorimeter cell 34.

The user may then use the depth gauge clamp 74 and depth clamp socket 86 to ensure the protruding instrument tip 24 is set at the correct depth for the cell container 58, as shown FIG. 11.

The electrosurgical instrument 16 to which the depth gauge clamp 74 is attached is now placed onto electrosurgical instrument calorimeter 30 using the stand 82 and instrument guide clamp 84. The instrument tip 24 is inserted into the cell container 58 through the passageway 72 and the depth gauge clamp 74 is positioned in contact with the lid 52.

In the case of, later, requiring the electrosurgical instrument 16 for use in a sterile environment, the detachable cell container 58, the attachment 60 and the lid 52 are considered an aid to preserving sterility because they may be easily exchanged for new, sterile units.

After appropriate parameters are configured by the user the invention is ready to make power and energy measurements.

Figure 17:
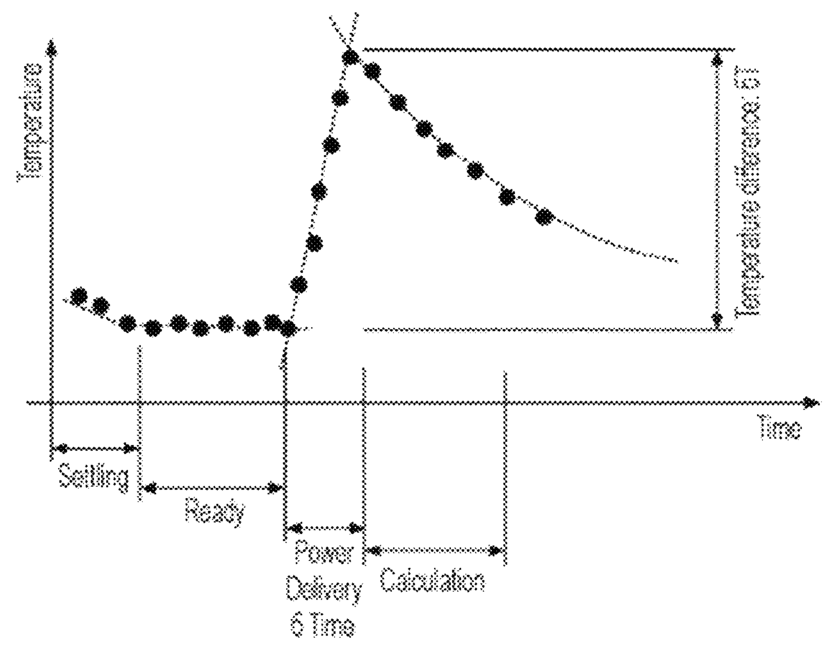
FIG. 17 shows a diagram depicting the different phases of a calorimetry measurement with respect to a temporal change of the temperature of a liquid.

FIG. 17 shows an exaggerated diagram of temperature measurements that are made when microwave power is applied to the electrosurgical instrument 16 and how these measurements relate to the calculated energy and power. Four distinct operational phases are shown in the measurement process.

Settling period: where the stirrer 50 is turned on to mix the liquid to equalise its temperature both between successive samples and from a diversity of temperature sensors 66.

Ready period: where the electrosurgical instrument calorimeter 30, in particular the controller 48, has detected that the variance in temperature measurements is sufficiently low to estimate that a temperature equilibrium is reached which indicates a reliable starting temperature. A signal is presented to the user that the electrosurgical instrument calorimeter 30 is ready to proceed.

Power delivery, or heating period: where microwave energy is supplied to the electrosurgical instrument 16 and absorbed by the liquid. Power delivery may by continuous, at a fixed level, of a variable level, or in bursts. These details may be set at the generator 12.

Calculation: where the power delivery is halted, either by command or detection by the electrosurgical instrument calorimeter 30 (for example using the signal cable 88) and a cooling curve can be established. Calculation takes the form of measuring the increase in temperature in a known amount of time into a known amount of liquid with a known specific heat capacity. The cooling curve is largely of a negative exponential form.

While it is possible that simply maximum and minimum recorded temperatures might be used to compute the temperature increase, the invention may also use a more accurate method. Three curves may be established: a) the linear or negative exponential curve is fitted to the Ready measurements, b) the largely linear slope and intercept of the relatively rapid Power delivery measurements, an/or c) the linear or negative exponential curve fitted to the Calculation period measurements.

The intersection points of these curves with each other and refined by accurate timestamps by the controller 48, will allow more data to be included into the final calculations which can be readily calculated by the calorimeter software.

The following formulae are used as the basis of the calorimeter's software to calculate the amount of energy and power delivered by the instrument.

$$Q=\Delta T\times M\times C \quad \text{(Eqn. 1)}$$

ΔT is the temperature change in degrees Celsius or Kelvin. M is the mass of the liquid in grams, and C is the heat capacity of the liquid in J $kg^{-1}$ $K^{-1}$. These are multiplied to give the heat energy added in Joules. Dividing this by the time span over which energy was supplied: t in seconds, gives the average power input value, P in Watts.

$$P=Q/t \quad \text{(Eqn. 2)}$$

Example: if power is applied to 200 g of water for 30 seconds causing a temperature increase of 2 degrees Celsius (or Kelvin).

$$2(K)\times 0.20\ (kg)\times 4184\ (J\ kg^{-1}K^{-1})=1673.6\ (J) \quad \text{(Eqn. 3)}$$

$$1673.6\ (J)/30\ (s)=55.787\ (W) \quad \text{(Eqn. 4)}$$

Figure 18:
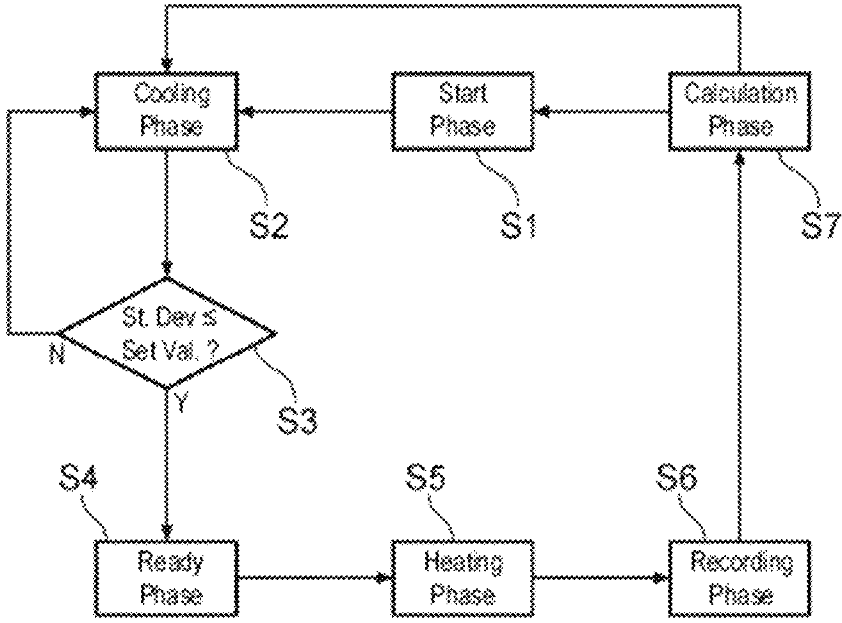
FIG. 18 shows a block diagram of a method for measuring an electromagnetic power output of the electrosurgical instrument.

A prototype control and measurement system may be implemented using an Arduino™ processor and coded in C++. The code is split into seven different phases, blocks or steps as shown in FIG. 18.

Step S1 is the start phase where the display 38 is turned on and the motor 42 is tested. Furthermore, in this phase the mass of liquid being used, the heat capacity of the liquid and the time of the experiment can be set allowing the electrosurgical instrument calorimeter 30 to be more adaptable and use different liquids and volumes of those liquids.

Step S2 is the cooling phase where the electrosurgical instrument calorimeter 30 may take a standard deviation of the previous temperature measurements. In addition, the motor 42 is turned on to rotate the stirrer 50 such that the thermal energy is equally distributed in the liquid.

In step S3, it is decided if the standard deviation determined in Step S2 is equal to or less than a set value. If yes, the method proceeds with step S4 and will move on to the Ready stage. If the standard deviation is more than the set value, then the process returns to step S2 which is repeated until the standard deviation is equal to or less than a set value.

Step S4 corresponds to the Ready phase and acts as a pause in the process before moving to the heating phase in step S5. To move on the step S5, the user may press a go button and/or actuates the external user interface 78.

The heating phase of step S5 is where the generator 12 is turned on and the initial temperature average is recorded by the at least one temperature sensor 66, along with a start timestamp. The heating phase ends when the set time is reached. During this phase if the reset button is held the test will end prematurely and the electrosurgical instrument calorimeter 30 will return to the start phase (step S1). The electrosurgical instrument calorimeter 30 takes averages of the initial and final temperatures to try to reduce the error.

After a set duration during cooling, the recording (or calculation) phase of step S6 is entered where the motor 42 may be turned off and the total time and average final temperature is recorded.

In the calculation phase in step S7 the electrosurgical instrument calorimeter 30 uses the data recorded to work out the power and energy input into the water from the instrument. These values are then displayed on the screen. The process can either then be repeated by pressing go again (which moves the process to step S2) or returned to the start screen by pressing reset (which moves the process to step S1).

The electrosurgical instrument calorimeter 30 can capture precise temperature measurements over a long period of time which presents the ability to record data about its own environment. Addition of an ambient air temperature sensor 92 can allow a correction factor to be applied throughout or after the measurement process to account for more rapid cooling in a cold ambient environment, thus improving the accuracy of the result. The ambient air temperature sensor 92 may be arranged exposed to the surroundings of the electrosurgical instrument calorimeter 30 as depicted in FIGS. 2 and 3 or may placed inside the housing 54. The ambient air temperature sensor 92 is optionally connected to the controller 48 and may be a temperature sensor similar to the temperature sensor 66.

The electrosurgical instrument calorimeter 30 may also be able to measure the increase in temperature of the liquid in response to mechanical energy supplied by the stirrer 50, especially with a variety of stirrer speeds and stirrer shapes. A correction factor may be formed by estimating the mechanical energy supplied by the stirrer 50 during a measurement, improving the accuracy of the result. This approximation can be executed by the controller 48, for example based on algorithm stored on the controller 48. To this end, the controller 48 may read the current motor speed.

The controller 48 may be instructed to establish a curve fit to temperature measurements before and after an electrosurgical instrument 16 is introduced into the liquid, thereby allowing an estimate of the amount of heat energy absorbed by the material of the instrument electrosurgical instrument 16. This may be added to the measurement result, improving its accuracy. A variety of electrosurgical instruments 16 might each require a variety of correction factors and might be automatically applied, for example after using the self-provisioning of parameters (see above).

Some electrosurgical instruments 16 can deliver more than a single electromagnetic frequency, either simultaneously, or in sequential order. For example, the Creo medical CROMA system may deliver both 5.8 GHz microwave power of up to 60 W and RF power of up to 200 W simultaneously. The electrosurgical instrument calorimeter 30 may be able to measure the combined output of all electromagnetic power delivered through the instrument tip 24 of the electrosurgical instrument 16 into the liquid tissue analog. In this case, an appropriate choice of liquid would be saline solution which readily absorbs radiated, conducted and capacitively coupled energy.

Figure 19:
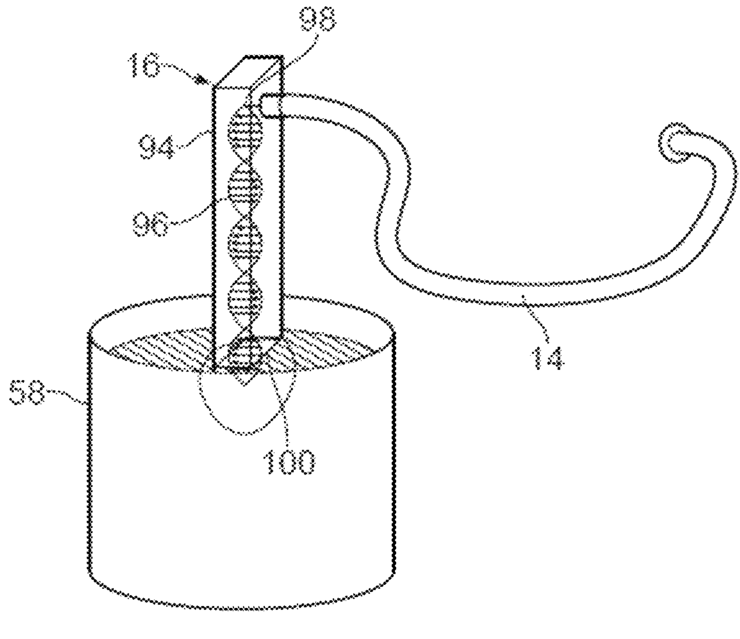
FIG. 19 shows a perspective view of another embodiment of the electrosurgical instrument placed over the liquid in the cell container.

By means of providing alternative lids 52, or no lid at all, a range of larger electrosurgical instruments 16 may be accommodated, for example a closed, open-ended or loaded, rigid or flexible microwave or mm-wave waveguide applicator 94 (see FIG. 19) that could be used to treat tissue surfaces. Waveguides applicators 94 would normally present a larger, flat surface area than coaxial cables and may necessitate the waveguide applicator 94 being held at the surface of the calorimeter liquid rather than being submerged, as shown in FIG. 19. The waveguide applicator 94 may include a waveguide 96 in which an antenna 98 is arranged. The antenna 98 is connected to the cable 14 and emits microwave and/or mm-wave radiation into the waveguide 96. The emitted radiation exits the waveguide 96 at a waveguide opening 100 which is an example of an energy output port. For calorimetry measurements, the waveguide opening 100 is placed directly above the liquid such that most of the emitted electromagnetic radiation, preferably all emitted electromagnetic radiation, is absorbed by the liquid.

Figure 20:
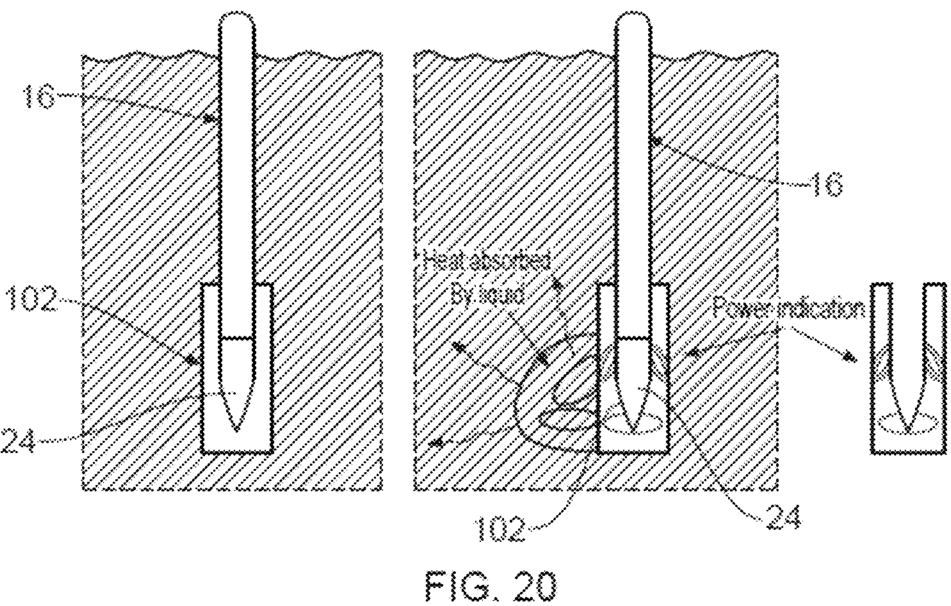
FIG. 20 shows a cross-sectional view of a heat sensitive load material placed around an instrument tip of the electrosurgical instrument of FIG. 1 before (left) and after (right) the emission of electromagnetic radiation.

The electrosurgical instrument calorimeter 30 may also be used in combination with a heat sensitive load material 102, such as a heat-sensitive gel, tape, or other material indicator. The heat sensitive load material 102 may be placed around the instrument tip 24 prior to power delivery into the electrosurgical instrument calorimeter 30. The heat sensitive load material 102 could provide information on the distribution of the energy profile around the geometry of the instrument tip 24, which is an important feature when using the electrosurgical instrument 16 for treatment. The heat sensitive load material 102 may be of a type that changes colour upon heating, or perhaps changes from a gel-state to a solid-state, or vice versa in the case of e.g., wax. If the heat sensitive load material 102 is used, then the calorimeter calculations may also include an additional term that allows for the specific heat capacity and mass of the heat sensitive load material 102 to be accounted for. If the material of the heat sensitive load material 102 is thin or lightweight in comparison to the mass of the calorimeter liquid, then it may not be necessary to account for the heating of the additional material indicator. FIG. 20 shows an example of using a heat indicator material to show the radiation pattern of the instrument.

The electrosurgical instrument calorimeter 30 may have a detachable cell container 58 and an attachment 60 which lend itself to operation in a sterile environment. In the case where an instrument performance is to be measured by the electrosurgical instrument calorimeter 30 and later used in a sterile environment, e.g., in-vivo operation, then the use of a detachable liquid cell 34 and inclusion of a detachable depth gauge socket 86 and lid 52 would facilitate the preservation of sterile conditions.

The electrosurgical instrument calorimeter 30 may contain various other mechanical features that may improve its usability or accuracy including, but not limited to: robotic placement of the electrosurgical instrument 16, data logging to a memory card or network server, audible alarms including voiced output of results and instructions, automatic power-off if used on battery power or DC/mains power, automatic replenishment of liquid that has become too warm via combinations of valves, pumps, tubing and heatsinks, remote servicing and data acquisition via internet link, a method measuring the mass of liquid in the calorimeter cell 34, such as an electronic balance, and microswitches to detect correct placement of the electrosurgical instrument 16 and lid 52.

Figure 21:
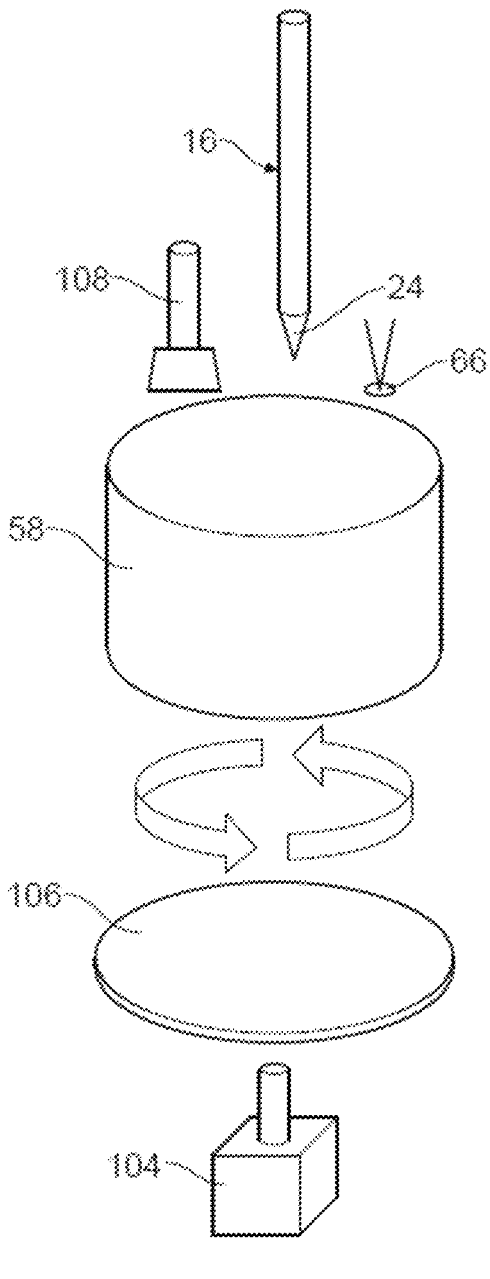
FIG. 21 shows an exploded view of another embodiment of the electrosurgical instrument calorimeter.

FIG. 21 refers to a further embodiment of the electrosurgical instrument calorimeter 32 in which stirring of the liquid within the calorimeter cell 34 is achieved in a different way. All other features of the electrosurgical instrument calorimeter 32 can be the same as discussed in conjunction with the other embodiments unless explicitly stated otherwise.

A motor 42 for rotating a stirrer 50 may not be present in this embodiment. Alternatively or additionally, a stirrer motor 104 is provided which is configured to move the calorimeter cell 34. In the embodiment depicted in FIG. 21, the stirrer motor 104 produces a rotational movement for rotating the cell container 58. In practice, the stirrer motor 104 may rotate the attachment 60 to which the cell container 58 is connected. To this end, a spinning disk 106 is attached to an axle of the stirrer motor 104. The attachment 60 and/or the cell container 58 are placed and releasably attached to the spinning disk 106 for rotating the cell container 58. The stirrer motor 104 may include features and/or characteristics similar to ones of the motor 42. In particular, the stirrer motor 104 may be controlled by the controller 48. In this embodiment, the lid 52 may not include the transmission means such that the lid 52 may have a simpler configuration.

In order to stir the liquid in the cell container 58, a stirring means 108 may be provided which does not move with the cell container 58. For example, the stirring means 108 may be steady with regard to the calorimeter base 32. The lid 52 may be arranged spaced apart from the calorimeter cell 34 such that the calorimeter cell 34 can move (rotate) with respect to the lid 52. Alternatively, one or more bearing elements may be included which allow the lid 52 to physically connect to the cell 34 but also facilitate relative movement between the lid 52 and cell 34. The stirring means 108 may be attached to the lid 52. The stirring means 108 may include a paddle. The stirring means 108 moves relative to the moved liquid in the moving cell container 58 such that the stirring means 108 stirs the liquid. The temperature sensor 66 may also be attached to the lid 52. The electrosurgical instrument 16 is arranged immovable with respect to the moving calorimeter cell 32. Thus, the temperature sensor 66 and/or the electrosurgical instrument 16 may also stir the liquid when the calorimeter cell 32 is moving.

Figure 22:
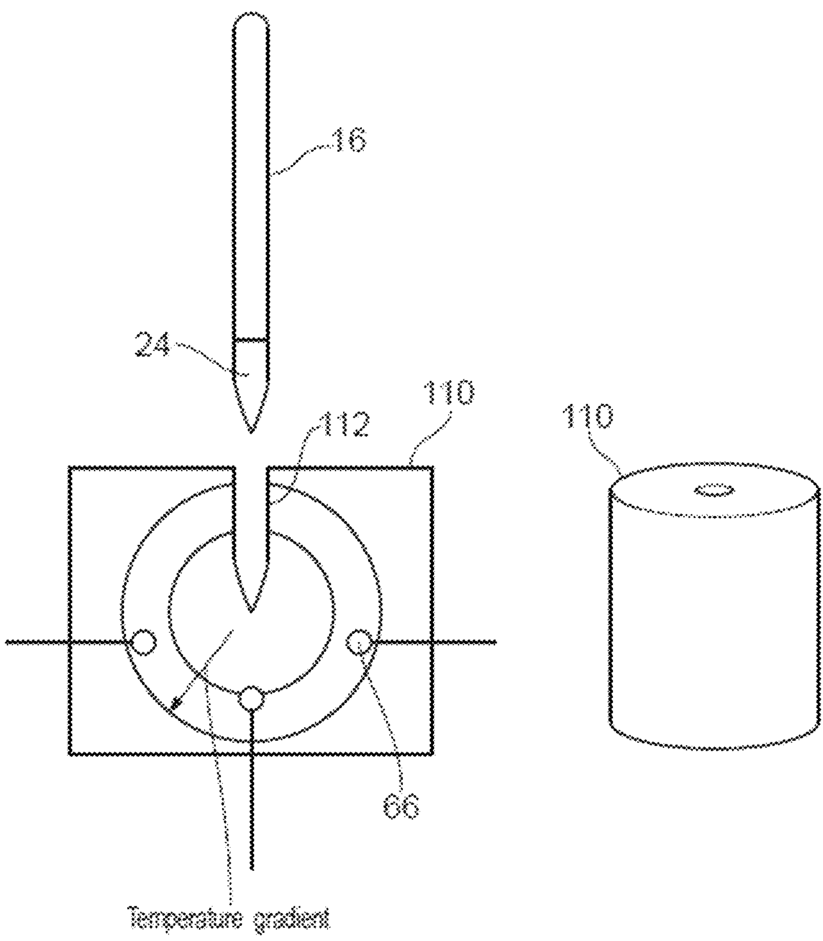
FIG. 22 shows a cross-sectional view (left) and a perspective view of a solid absorption material.

The embodiment depicted in FIG. 22 relates to another embodiment of the absorption material 110 which includes a solid, for example a Radiation Absorptive Material (RAM) such as is used in microwave attenuators and microwave anechoic chambers. Typical materials that are used in making RAM are homogeneous mixes of iron ferrite, conductive carbon black, graphite, carbonyl iron, or carbon nanotubes. The solid absorption material 110 has an outer shape which corresponds to the inner shape of the cell container 58. In particular, the other diameter of the solid absorption material 110 is slightly smaller than the inner diameter of the cell container 58 such that the solid absorption material 110 can be tightly inserted into the cell container 58.

The solid absorption material 110 includes a material socket 112 for receiving the instrument tip 24 of the electrosurgical instrument 12. The shape of the material socket 112 is adapted to the shape of the instrument tip 24. Optionally, a plurality of solid absorption materials 110 are provided, wherein each solid absorption material 110 has the same outer shape but differ in the shape of the material socket 112. Each solid absorption material 110 has a material socket 112 which is adapted to receive a different type of electrosurgical instrument 12.

Optionally, the solid absorption material 110 includes the at least one temperature sensor 66. Preferably, a plurality of temperature sensors 66 are provided allowing the measurement of a temperature gradient with the solid absorption material 110. The temperature gradient is generated by the absorption of the electromagnetic radiation emitted by the instrument tip 24. The measured temperature change and/or the temperature gradient may be used to determine the absorbed electromagnetic energy or power. In addition, the temperature gradient allows to determine an emission profile of the instrument tip 24.

Figure 23:
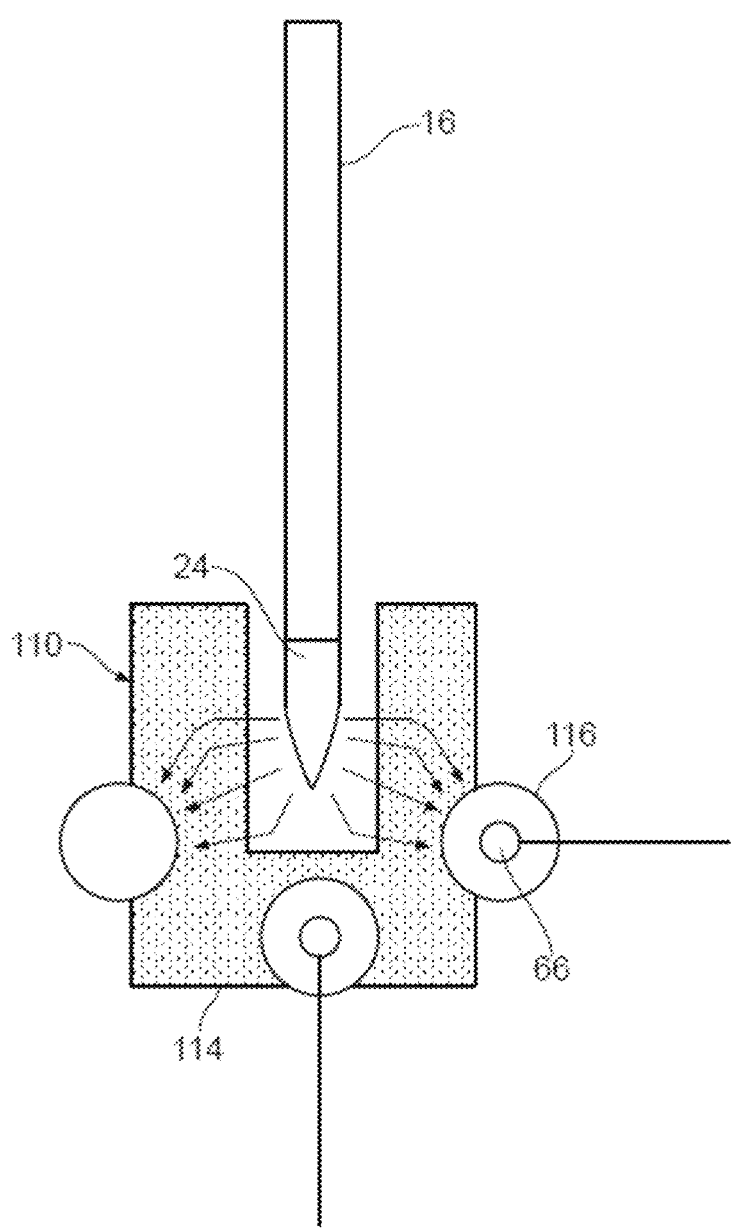
FIG. 23 shows a cross-sectional view of another embodiment of the absorption material.

The embodiment depicted in FIG. 23 relates to another embodiment of the absorption material 110 which includes a metamaterial 114 and an absorber 116. The meta material 114 is configured to guide or focus the electromagnetic radiation emitted by the instrument tip 24 to the absorber 116 (as indicated by the arrows in FIG. 23). The absorber 116 absorbs the electromagnetic radiation resulting in a heating of the absorber 116. This temperature change is measured using the temperature sensor 66 which may be arranged within the absorber 116. The meta material 114 may be shaped to be inserted into the cell container 58 and includes a socket for receiving the instrument tip 24. However, in this embodiment, the socket may not be shaped to match the instrument tip 24. In fact, an air gap may be arranged between the instrument tip 24 and the meta material 114. The guiding properties of the meta material 114 allow to direct basically all of the emitted electromagnetic radiation to the absorber 116.

The invention claimed is:

1. An electrosurgical instrument calorimeter for measuring an electromagnetic energy output of an electrosurgical instrument powered by a generator, the electrosurgical instrument including an instrument tip configured to radiate the electromagnetic energy into a target tissue at a target site for obtaining a treatment effect, the electrosurgical instrument calorimeter comprising a calorimeter cell for containing an absorption material configured to absorb electromagnetic radiation, at least one temperature sensor configured to measure a temperature of the absorption material, and a support structure configured to hold the electrosurgical instrument in such a position that the instrument tip is inserted in the absorption material such that electromagnetic radiation emitted by the instrument tip is absorbed by the absorption material.

2. The electrosurgical instrument calorimeter of claim 1, further comprising a calorimeter base, wherein the calorimeter cell is attached to the calorimeter base.

3. The electrosurgical instrument calorimeter of claim 2, wherein the calorimeter cell includes a cell housing attached to the calorimeter base, an attachment configured to be releasably attached to the cell housing, and a cell container configured to receive the absorption material and be arranged within the cell housing.

4. The electrosurgical instrument calorimeter of claim 3, wherein the cell housing and/or the cell container provide heat insulation for the absorption material and/or the at least one temperature sensor is arranged within and/or on the cell container.

5. The electrosurgical instrument calorimeter of claim 3, wherein the calorimeter cell includes a first electrical connector attached to the cell housing and a second electrical connector attached to the attachment and in electrical connection with the at least one temperature sensor, wherein insertion of the attachment into the cell housing connects the second electrical connector to the first electrical connector.

6. The electrosurgical instrument calorimeter of claim 3, wherein the calorimeter cell further includes a lid for closing the calorimeter cell, wherein the lid includes a passageway for inserting the electrosurgical instrument into the absorption material.

7. The electrosurgical instrument calorimeter of claim 6, wherein the absorption material is a liquid or a powder, wherein the electrosurgical instrument calorimeter further comprises a stirrer for stirring the liquid or the powder, wherein the stirrer is attached to the lid.

8. The electrosurgical instrument calorimeter of claim 7, further comprising a motor for moving the stirrer, wherein the cell housing further includes a motor bracket for supporting the motor, and wherein the lid includes a transmission device for transmitting a motion of the motor to the stirrer.

9. The electrosurgical instrument calorimeter of claim 1, wherein the absorption material is a liquid or a powder, wherein the electrosurgical instrument calorimeter further comprises a stirrer motor configured to move the calorimeter cell for stirring the liquid or the powder.

10. The electrosurgical instrument calorimeter of claim 1, wherein the absorption material is a solid, wherein the at least one temperature sensor is arranged within the solid absorption material.

11. The electrosurgical instrument calorimeter of claim 2, wherein the support structure is supported by the calorimeter base, wherein the support structure includes an instrument guide clamp for holding the electrosurgical instrument in an upright position and a stand for supporting the instrument guide clamp, the stand being attached to the calorimeter base.

12. The electrosurgical instrument calorimeter of claim 6, further comprising a depth gauge mechanism for facilitating a repeatably consistent placement of the instrument tip of the electrosurgical instrument in the absorption material, wherein the depth gauge mechanism includes a depth gauge clamp which can be attached to the electrosurgical instrument and has an outer diameter larger than a diameter of the passageway and a depth gauge socket having a depth that corresponds to a distance between a distal end of the electrosurgical instrument and an upper surface of the lid in the repeatably consistent placement of the electrosurgical instrument.

13. The electrosurgical instrument calorimeter of claim 12, wherein the depth gauge socket is arranged on the calorimeter base.

14. The electrosurgical instrument calorimeter of claim 8, further comprising a controller configured to calculate the electromagnetic energy output of the electrosurgical instrument based on a measurement of the at least one temperature sensor, wherein the controller is additionally configured to control the motor, and/or the electrosurgical instrument calorimeter includes at least one control connector configured to provide an electrical connection between the controller and the generator for providing an electronic communication between the controller and the generator.

15. The electrosurgical instrument calorimeter of claim 14, further comprising an external user interface connectable to the controller and/or the generator for controlling emission of the electromagnetic energy output of the electrosurgical instrument and/or the measurement of the temperature of the absorption material.

16. The electrosurgical instrument calorimeter of claim 14, further comprising an automated test equipment system connectable to the controller and connectable to the generator, wherein the automated test equipment system is configured to communicate with the controller and the generator for performing automated calorimetry measurements.

17. The electrosurgical instrument calorimeter of claim 3, further comprising a return electrode which is arranged in the cell container, the return electrode being electrically grounded, and/or a radiation detector arranged in the calorimeter cell and configured to detect electromagnetic radiation, and/or an ambient air temperature sensor configured to measure a temperature of ambient air surrounding the electrosurgical instrument calorimeter.

18. The electrosurgical instrument calorimeter of claim 1, further comprising a heat sensitive load material which is configured to be placed around the instrument tip of the electrosurgical instrument and which is configured to locally change a physical property upon irradiation of electromagnetic radiation, wherein the heat sensitive load material is configured to locally change a physical property depending on a strength and/or a duration of the electromagnetic radiation.

19. A method for measuring an electromagnetic energy output of an electrosurgical instrument powered by a generator, the electrosurgical instrument including an instrument tip configured to radiate the electromagnetic energy into a target tissue at a target site for obtaining a treatment effect, the method comprising steps of:

a) filling a predetermined amount of an absorption material in a calorimeter cell of an electrosurgical instrument calorimeter, the absorption material configured to absorb electromagnetic radiation, b) placing the electrosurgical instrument in such a position that the instrument tip is inserted in the absorption material such that electromagnetic radiation emitted by the electrosurgical instrument is absorbed by the absorption material, c) operating the electrosurgical instrument for a predetermined time span to emit electromagnetic radiation into the absorption material, d) measuring a temperature change of the absorption material, and e) calculating an energy of the electromagnetic radiation emitted by the electrosurgical instrument based on the measured temperature change.

20. The method of claim 19, wherein step b) includes inserting the instrument tip into a depth gauge socket, attaching a depth gauge clamp to the electrosurgical instrument such that the depth gauge clamp is in contact with an opening of the depth gauge socket, closing the calorimeter cell with a lid, and inserting the instrument tip into a passageway of the lid until the depth gauge clamp abuts against the lid.

21. The method of claim 19, wherein step b) further includes holding the electrosurgical instrument in a fixed relationship with respect to the calorimeter cell using a support structure.

22. The method of claim 19, wherein step b) includes placing an energy output port of a waveguide of the electrosurgical instrument close to the absorption material.

23. The method of claim 19, wherein step c) is executed after the temperature of the absorption material reaches a substantially equilibrium temperature, wherein the temperature change is recorded with respect to the substantially equilibrium temperature.

24. The method of claim 19, wherein the absorption material is a liquid or a powder, wherein the method further comprises stirring the liquid or the powder in the calorimeter cell.

25. The method of claim 19, wherein steps c) and d) are automatically executed after receiving a start signal, wherein a controller of the electrosurgical instrument calorimeter and the generator are connected to each other, wherein the start signal is generated by an external user interface that is connected to the controller and/or the generator or by an automated test equipment system that is connected to the controller and/or the generator.

26. The method of claim 24, wherein step d) is used to detect execution of step c), and/or wherein presence of electromagnetic radiation within the calorimeter cell is detected, wherein the execution of steps c), d) and/or e) is stopped or prohibited if an intensity of the detected electromagnetic radiation is above a predetermined threshold, and/or wherein the calculation of step e) is further based on a temperature of ambient air surrounding the electrosurgical instrument calorimeter, the energy introduced by a stirrer stirring the liquid or the powder, and/or the heat absorption of the electrosurgical instrument.

27. The method of claim 19, wherein a heat sensitive load material is placed around the instrument tip of the electrosurgical instrument, the electrosurgical instrument is operated or steps b) and c) are executed, and a radiation pattern of the instrument tip of the electrosurgical instrument is identified by a local change of a physical property of the heat sensitive load material induced by the irradiation of electromagnetic radiation emitted by the instrument tip.

28. The method of claim 27, wherein the calculation of step e) is further based on a specific heat capacity of the heat sensitive load material and/or the mass of the heat sensitive load material.

* * * * *